United States Patent
Holden et al.

(10) Patent No.: US 10,191,300 B2
(45) Date of Patent: Jan. 29, 2019

(54) OPHTHALMIC OPTICAL LENS FOR VISION CORRECTION HAVING ONE OR MORE AREAS OF MORE POSITIVE POWER

(71) Applicant: BRIEN HOLDEN VISION INSTITUTE, Sydney, New South Wales (AU)

(72) Inventors: Brien Anthony Holden, Kensington (AU); Padmaja Rajagopal Sankaridurg, Maroubra (AU); Klaus Ehrmann, Queenscliffe (AU); Fabian Conrad, Maroubra (AU); Arthur Ho, Randwick (AU)

(73) Assignee: Brien Holden Vision Institute, Sydney, New South Wales (AU)

( * ) Notice: Subject to any disclaimer, the term of this patent is extended or adjusted under 35 U.S.C. 154(b) by 0 days.

(21) Appl. No.: 14/650,196

(22) PCT Filed: Dec. 10, 2013

(86) PCT No.: PCT/AU2013/001437
§ 371 (c)(1),
(2) Date: Jun. 5, 2015

(87) PCT Pub. No.: WO2014/089612
PCT Pub. Date: Jun. 19, 2014

(65) Prior Publication Data
US 2015/0316788 A1    Nov. 5, 2015

Related U.S. Application Data

(60) Provisional application No. 61/889,189, filed on Oct. 10, 2013.

(30) Foreign Application Priority Data

Dec. 10, 2012    (AU) ................. 2012905371

(51) Int. Cl.
G02C 7/00    (2006.01)
G02C 7/02    (2006.01)
(Continued)

(52) U.S. Cl.
CPC ............ *G02C 7/044* (2013.01); *A61F 2/1451* (2015.04); *A61F 2/16* (2013.01); *G02C 7/041* (2013.01);
(Continued)

(58) Field of Classification Search
CPC ........ G02C 7/061; G02C 7/063; G02C 7/066; G02C 7/06
(Continued)

(56) References Cited

U.S. PATENT DOCUMENTS 6,260,966 B1   7/2001  Sawano et al.
2008/0284977 A1  11/2008  Huang
(Continued)

FOREIGN PATENT DOCUMENTS

CN    102119354 A    7/2011
DE    102009053467   7/2010
(Continued)

OTHER PUBLICATIONS

International Search Report for PCT/AU2013/001437, filed Feb. 11, 2014; ISA/AU.

*Primary Examiner* — Mahidere Sahle
(74) *Attorney, Agent, or Firm* — Jones Day

(57) ABSTRACT

The present disclosure is directed to lens, methods of making, designing lens and/or methods using lens in which performance may be improved by providing one or more steps in the central portion of the optical zone and one or more steps in the peripheral portion of the optic zone. In
(Continued)

some embodiments, such lens may be useful for correcting refractive error of an eye and/or for controlling eye growth.

20 Claims, 11 Drawing Sheets

(51) Int. Cl.
*G02C 7/06* (2006.01)
*G02C 7/04* (2006.01)
*A61F 2/14* (2006.01)
*A61F 2/16* (2006.01)

(52) U.S. Cl.
CPC ......... *G02C 7/066* (2013.01); *G02C 2202/24* (2013.01)

(58) Field of Classification Search
USPC .............................................. 351/159.42, 169
See application file for complete search history.

(56) References Cited

U.S. PATENT DOCUMENTS

| | | |
|---|---|---|
| 2009/0213325 A1 | 8/2009 | Katzman et al. |
| 2009/0323020 A1 | 12/2009 | Zhao et al. |
| 2010/0036489 A1 | 2/2010 | Lindacher et al. |
| 2011/0181834 A1* | 7/2011 | Gerbaud ................ G02C 7/061 351/159.42 |
| 2014/0036172 A1* | 2/2014 | Trajkovska-Broach .................... G02C 7/083 349/13 |

FOREIGN PATENT DOCUMENTS

| | | |
|---|---|---|
| DE | 102012018898 | 4/2013 |
| JP | 2004294456 | 10/2004 |
| JP | 2011530726 | 12/2011 |
| WO | WO 00/46629 | 8/2000 |
| WO | WO 2010019397 | 2/2010 |
| WO | WO 2011060176 | 5/2011 |

* cited by examiner

OPHTHALMIC OPTICAL LENS FOR VISION CORRECTION HAVING ONE OR MORE AREAS OF MORE POSITIVE POWER

CROSS REFERENCE TO RELATED APPLICATIONS

This application is a U.S. National Phase Application under 35 U.S.C. 371 of International Application No. PCT/AU2013/001437 filed on Dec. 10, 2013 and published in English as WO 2014/089612 on Jun. 19, 2014. This application is based on and claims the benefit of Australian Provisional Application No. 2012905371, filed Dec. 10, 2012, entitled "Optical Lens for Vision Correction Having One or More Areas of More Positive Power" and U.S. Provisional Application No. 61/889,189, filed Oct. 10, 2013 entitled "Ophthalmic Optical Lens for Vision Correction Having One or More Areas of More Positive Power". The entire disclosures of all of the above applications are incorporated herein by reference in their entirety.

FIELD

This disclosure relates to ophthalmic optical lenses designed to correct refractive errors of an eye and/or to control eye growth and/or additionally having one or more areas of more positive power, and methods of using such ophthalmic optical lens designs. This disclosure also relates to ophthalmic optical lenses designed to correct refractive errors of an eye and having one or more areas of more positive power. Certain embodiments may be applied to or realized as, for example, contact lenses, intraocular lenses, corneal onlays and corneal inlays, and/or can be applied to or used to at least reduce refractive errors of the eye such as myopia, hyperopia, astigmatism and presbyopia, but is of particular interest in relation to contact lenses, especially to provide contact lenses designed for correction of myopia and/or control of the progression of myopia. Certain embodiments may be applied to or realized as, for example, contact lenses, intraocular lenses, corneal onlays and corneal inlays, and/or can be applied to, especially optically connected to, the eye for the correction of presbyopia. In some embodiments, the disclosure is applicable to or is realized as bifocal and/or multifocal contact lenses.

BACKGROUND

A basic bifocal or multifocal ophthalmic lens such as an intraocular lens, a corneal onlay, a corneal inlay, or a contact lens has a central area of the optical zone with an optical power that provides distance vision and an annular area about the central area with a power that gives near vision (i.e. center-distance bifocals or multifocals). Another basic bifocal or multifocal ophthalmic lens has a central area of the optical zone with an optical power that provides near vision and an annular area about the central area with a power that gives distance vision (i.e. center-near bifocals or multifocals). The optical zone of a contact lens may be approximately the size of the pupil. The pupil diameter may vary in the range 3 mm to 8 mm and the optical zone size of a contact lens may be selected accordingly. Some contact lenses designed for controlling the progression of myopia or correcting presbyopia rely on the use of an optical power in at least one area of the optical zone that is relatively positive compared to the distance power, wherein the distance power is for example defined as a power of a lens required to provide the appropriate refractive correction to the eye when the eye is viewing distant visual objects. The one or more areas of this relatively more positive power can be located centrally or in the periphery of the optical zone or both, wherein periphery is for example the zone of the contact lens that lies at a greater distance from the optical axis than the central zone and/or the area with an optical power providing distance vision.

The presence of additional relatively positive power in the optical zone of the contact lens is often reported by wearers to be causing effects that diminish vision performance or visual performance. Such effects include subjective complaints of doubling, ghosting, looking through a fish bowl (i.e. distortion) and/or in some instances a decrease in high and low contrast visual acuity. A decrease in low contrast visual acuity may also be reported as a decrease in contrast. A decrease in contrast may be identified and/or measured as a loss in contrast sensitivity.

It is an object of the present disclosure to provide an ophthalmic lens that for the wearer results in suitable or improved vision performance or visual performance in one or more aspects of vision performance or visual performance. It is also an object of the present disclosure to provide an ophthalmic lens that for the wearer results in suitable or improvement in vision performance or visual performance and has additional relatively positive power compared to distance power in the optical zone. It is also an object of the present disclosure to provide an ophthalmic lens that corrects refractive errors of an eye and has one or more areas of relatively positive power in the optical zone. It is another object of the present disclosure to provide an ophthalmic lens that corrects refractive errors of an eye, has one or more areas of relatively positive power compared to distance power in the optical zone and provides suitable or improved visual performance or vision performance in one or more aspects of vision performance. Combinations of one or more of these objectives are also contemplated. It is also an object of the present disclosure to provide methods of using such lens. Suitable or improvement in vision performance or visual performance may be one or more of the following: clarity of vision, degree of doubling, degree of ghosting, distortion, contrast, contrast sensitivity, visual acuity and overall quality of vision.

The prior art lenses and methods have the drawback that with the addition of more positive power in the optic zone, then vision performance or visual performance is affected. The present disclosure is directed to overcome and/or ameliorate at least one of the disadvantages of the prior art as will become apparent from the discussion herein by providing more positive power in the optic zone by use of steps in one or more regions of the optic zone. This results in lenses that may be used both for correction of myopia and/or control of the progression of myopia. This also results in lenses that may be used to correct refractive errors of an eye such as myopia, hyperopia, astigmatism and/or presbyopia without substantially affecting one or more aspects of vision performance or visual performance, for example without substantially changing ghosting. This also results in lens that may be used to correct refractive errors of an eye with suitable or improvement in vision performance or visual performance and to control of eye growth. Accordingly, methods of designing, methods of use and lenses for solving these and other problems disclosed herein are desirable. The present disclosure is directed to overcome and/or ameliorate at least one of the disadvantages of the prior art as will become apparent from the discussion herein.

Reference to any prior art in the specification is not, and should not be taken as, an acknowledgment or form of a suggestion that this prior art forms part of the common general knowledge in Australia or other jurisdictions or that this prior art could reasonably be expected to be ascertained, understood and regarded as relevant by a person skilled in the art.

SUMMARY

It has been found that one or more of the aspects of visual performance or vision performance may be improved by providing one or more steps, two or more steps, or three or more steps, in the optical power transition between the areas of the optical zone having more negative and more positive optical powers. It has also been found that use of power profiles with step functions moderates distractive images leading to a positive effect to improve one or more of the aspects of visual performance or vision performance. Suitable or improvements in vision performance or visual performance may be one or more of the following: clarity of vision, degree of doubling, degree of ghosting, distortion, contrast, contrast sensitivity, visual acuity, and overall quality of vision. Clarity of vision may, for example, be assessed using a clinical questionnaire quantified by a 1 to 10 numerical rating scale where 1=extremely good clarity and 10=extremely poor clarity of vision. Degree of doubling may, for example, be assessed using a clinical questionnaire quantified by a 1 to 10 numerical rating scale where 1=no observable doubling of visual image and 10=extremely pronounced doubling of visual image. Degree of ghosting may, for example, be assessed using a clinical questionnaire quantified by a 1 to 10 numerical rating scale where 1=no observable ghosting associated with the visual image and 10=extremely pronounced ghosting associated with the visual image. Distortion may, for example, be assessed using a clinical questionnaire quantified by a 1 to 10 numerical rating scale where 1=no observable distortion of the visual image and 10=severe distortion of the visual image. Contrast may, for example, be assessed using a clinical questionnaire quantified by a 1 to 10 numerical rating scale where 1=extremely poor contrast in the visual image and 10=excellent contrast in the visual image. Contrast sensitivity may, for example, be measured using a contrast sensitivity test chart such as a letter-based contrast sensitivity chart (e.g. Pelli-Robson chart) or a since-wave grating based contrast sensitivity chart (e.g. Functional Acuity Contrast Test, or FACT, chart). Visual acuity may, for example, be measured using a visual acuity test chart such as a Snellen chart or a Bailey-Lovie chart, for which the test may be applied under high illumination or low illumination, and/or for which the chart may be high contrast, medium contrast, or low contrast. Overall quality of vision may, for example, be assessed using a clinical questionnaire quantified by a 1 to 10 numerical rating scale where 1=extremely good overall quality of vision and 10=extremely poor overall quality of vision.

In certain embodiments, one or more aspects of visual performance or vision performance may be positively affected or improved by providing one or more steps in the central portion of the optical zone and one or more steps in the peripheral portion of the optic zone. In certain embodiments, one or more aspects of visual performance or vision performance may be positively affected or improved by providing two or more steps in the central portion of the optical zone and two or more steps in the peripheral portion of the optic zone. In certain embodiments, one or more aspects of visual performance or vision performance may be positively affected or improved by providing two or more steps in the central portion of the optical zone and three or more steps in the peripheral portion of the optic zone. In certain embodiments, one or more aspects of visual performance or vision performance may be positively affected or improved by providing three or more steps in the central portion of the optical zone and three or more steps in the peripheral portion of the optic zone. In some embodiments, such lens designs may be useful for correcting refractive error of an eye and/or for controlling eye growth. In some embodiments, such lens designs may be useful for correction of myopia and for controlling of the progression of myopia. In some embodiments, such lens designs may be useful for correction of presbyopia. Presbyopia is the age-related progressive loss of the ability of the eye to accommodate thus resulting in blurred vision for near objects. It is said to be caused at least in part through hardening of the crystalline lens of the eye.

Certain embodiments of the present disclosure provide an ophthalmic optical lens for correcting a refractive error of an eye and to control eye growth including an optical zone with a primary area having an optical power and one or more secondary areas, including at least one peripherally of the primary area, having an optical power that is more positive relative to the optical power of the primary area, wherein between the primary area and the one or more secondary areas, the optical power progressively transitions between the more negative and more positive powers with at least one step, at least two steps, or at least three steps substantially between the primary and one or more secondary areas in which the magnitude (i.e. ignoring the sign or direction) of the rate of change of the power decreases and then increases by amounts and over a distance sufficient to provide suitable or improved vision performance or visual performance in one or more aspects of vision performance or visual performance. Suitable or improvement in vision performance or visual performance experienced with the lens may be one or more of the following: clarity of vision, degree of doubling, degree of ghosting, distortion, contrast, contrast sensitivity, visual acuity, and overall quality of vision. Clarity of vision may, for example, be assessed using a clinical questionnaire quantified by a 1 to 10 numerical rating scale where 1=extremely good clarity and 10=extremely poor clarity of vision. Degree of doubling may, for example, be assessed using a clinical questionnaire quantified by a 1 to 10 numerical rating scale where 1=no observable doubling of visual image and 10=extremely pronounced doubling of visual image. Degree of ghosting may, for example, be assessed using a clinical questionnaire quantified by a 1 to 10 numerical rating scale where 1=no observable ghosting associated with the visual image and 10=extremely pronounced ghosting associated with the visual image. Distortion may, for example, be assessed using a clinical questionnaire quantified by a 1 to 10 numerical rating scale where 1=no observable distortion of the visual image and 10=severe distortion of the visual image. Contrast may, for example, be assessed using a clinical questionnaire quantified by a 1 to 10 numerical rating scale where 1=extremely poor contrast in the visual image and 10=excellent contrast in the visual image. Contrast sensitivity may, for example, be measured using a contrast sensitivity test chart such as a letter-based contrast sensitivity chart (e.g. Pelli-Robson chart) or a since-wave grating based contrast sensitivity chart (e.g. Functional Acuity Contrast Test, or FACT, chart). Visual acuity may, for example, be measured using a visual acuity test chart such as a Snellen chart or a Bailey-Lovie chart, for which the test may be applied under high illumination or low illumination, and/or for which the chart may be high contrast, medium contrast, or low contrast. Overall quality of vision may, for example, be assessed using a clinical questionnaire quantified by a 1 to 10 numerical rating scale where 1=extremely good overall quality of vision and 10=extremely poor overall quality of vision.

The ophthalmic lens or ophthalmic system may be one or more of the following: a contact lens, an intraocular lens which may be an anterior chamber intraocular lens or a posterior chamber intraocular lens, a corneal onlay and a corneal inlay.

In certain embodiments, the optical power of the primary area is selected for myopia correction and has a distance power. In one or more embodiments, the secondary areas are arranged and their powers selected with the objective of controlling the progression of myopia. Myopia progresses through steady growth of the eye along the optical axis, causing the focal point to be in front of the retina.

In one or more embodiments, the optical power of the primary area is selected to provide distance, intermediate, or near correction for the eye, and the secondary areas have more positive powers than the primary area.

In some embodiments, said progressive transitioning of the optical power is continuous, at least to the extent of not having discontinuities in magnitude, but also to avoid discontinuities in the rate of change of power with respect to distance across the lens (i.e. a first derivative). In some embodiments, the progressive transitioning of the optical power is continuous or substantially continuous. By suitable or improved vision performance or visual performance herein is meant one or more of clarity of vision, degree of doubling, degree of ghosting, contrast, contrast sensitivity, visual acuity and overall quality of vision.

In one or more embodiments, there are one or more secondary areas centrally of the optical zone, as well as peripherally. In certain embodiments, the primary area may then be an annulus between central and peripheral secondary areas. In these embodiments, there may be at least one step as aforedescribed in each of the central and peripheral secondary areas and not including the primary and secondary areas. By locating one or more of the secondary areas centrally of the optical zone, for example, a simultaneous correction of different optical defects may be reached.

In some embodiments, there are at least two steps in a secondary area located peripherally of the primary area. Where there are two or more steps, the depths and/or the heights of the steps may each be equal or unequal. The depth and/or heights of the steps may for example be measured as the difference between an envelope of the surface of the lens and an actual surface of the lens. In other embodiments, where there are two or more steps, the depths and/or the heights of the steps may be one of the following: equal, substantially equal and unequal.

In one or more embodiments, the step may include a point, or a finite portion, in which the rate of change of the optical power is zero, i.e. the step is flat. In other embodiments, the rate of change may reverse in the step. In one or more embodiments, the step may include a point, or a finite portion, in which the rate of change of the optical power is zero or substantially zero, i.e. the step is flat or substantially flat. In other embodiments, the rate of change may reverse in the step.

In some embodiments, the rate of change of the optical power may be similar or the same before and after the step. In other embodiments, it may be different before and after the step. In some embodiments, there may be 1 to 5, 2 to 4, 1 to 3, 2 to 3, 2 to 5 or 2 to 6 radially spaced steps in the power transitions between one or more of the secondary areas and one or more of the primary areas. In some embodiments, there may be 1 to 5, 2 to 4, 1 to 3, 2 to 3, 2 to 5 or 2 to 6 radially spaced steps in the power transitions between secondary areas. Radially means in a direction towards or away from the centre of the optical axis. Radial distances may sometimes be referred to as half-chord distances. In some embodiments, there may be at least 2, 3, 4, 5 or 6 radially spaced steps in one or more of the secondary areas or each secondary area. In some embodiments, there may be at least 2 or 3 radially spaced steps in the central portion of the optical portion and at least 4 or 5 radially spaced steps in the peripheral portion of the optical portion. In some embodiments, there may be between 1 to 2 radially spaced steps in the central portion of the optical portion and between 2 to 6 radially spaced steps in the peripheral portion of the optical portion. In some embodiments, there may be between 2 to 3 radially spaced steps in the central portion of the optical portion and between 2 to 4 radially spaced steps in the peripheral portion of the optical portion. In some embodiments, there may be at least 2 or 3 radially spaced steps per mm of the optical portion of the lens. The use of a plurality of steps has for example an advantage of suitable or improved vision performance or visual performance in one or more aspects of vision performance or visual performance. In certain embodiments, the first power transition and the second power transition have between 1 to 5, 2 to 4, 1 to 3, 2 to 3, 2 to 5 or 2 to 6 radially spaced steps. In certain embodiments, wherein at least one of the first power transition and the second power transition have between 1 to 5, 2 to 4, 1 to 3, 2 to 3, 2 to 5 or 2 to 6 radially spaced steps between one or more of the secondary areas or between each secondary area. These steps may also be present in other power transitions. In certain embodiments, there is at least 2, 3, 4, 5 or 6 radially spaced steps between one or more of the secondary areas or between each secondary area.

Typically, the lens optics is substantially axially symmetric. In some embodiments, the lens optics may be laterally asymmetric and/or rotationally asymmetric. These different symmetries have different advantages, for example an asymmetric lens optics may partially compensate or correct for certain asymmetric optical defects or aberrations of the eye.

The peripheral secondary area may commence at a radius in the range 0.5 to 3 mm, 1 to 2 mm, or 1 to 1.5 mm.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

The present disclosure will now be further described, by way of example only, with reference to the accompanying drawings, in which.

DETAILED DESCRIPTION

The present disclosure is described in further detail with reference to one or more embodiments, some examples of which are illustrated in the accompanying drawings. The examples and embodiments are provided by way of explanation and are not to be taken as limiting to the scope of the disclosure. Furthermore, features illustrated or described as part of one embodiment may be used by themselves to provide other embodiments and features illustrated or described as part of one embodiment may be used with one or more other embodiments to provide further embodiments. The present disclosure covers these variations and embodiments as well as other variations and/or modifications.

The subject headings used in the detailed description are included for the ease of reference for the reader and should not be used to limit the subject matter found throughout the disclosure or the claims. The subject headings should not be used in construing the scope of the claims or the claim limitations.

As used herein, step may be defined as, for example, a region on a lens in which the power is monotonically changing over the region, as a location within the region over which the magnitude (i.e. ignoring the sign or direction) of the rate of change of the power over the region decreases and then increases. The rate of change of power within the location (i.e. within the step) may be zero (i.e. the power is constant along the step) or non-zero (i.e. the power continues to change along the step but at a lesser rate of change). A step may alternatively, be defined, for example, as a location over a lens in which the absolute value of the first derivative of power with respect to distance across a lens decreases and then increases.

Figure 1:
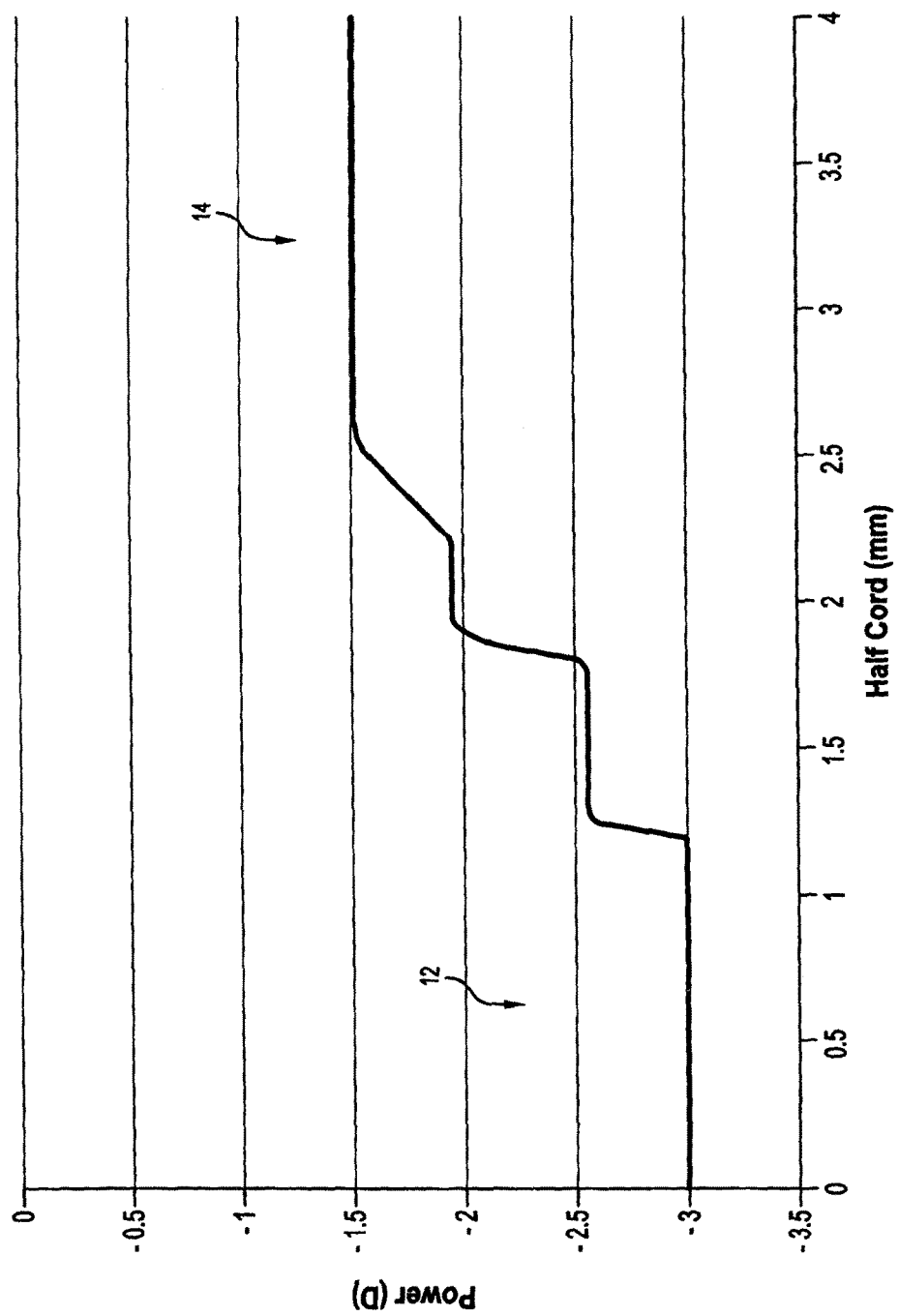
FIGS. 1 to 4 are half-chord optical power diagrams for respective axially symmetric contact lenses constituting respective embodiments of the present disclosure.
Figure 2:
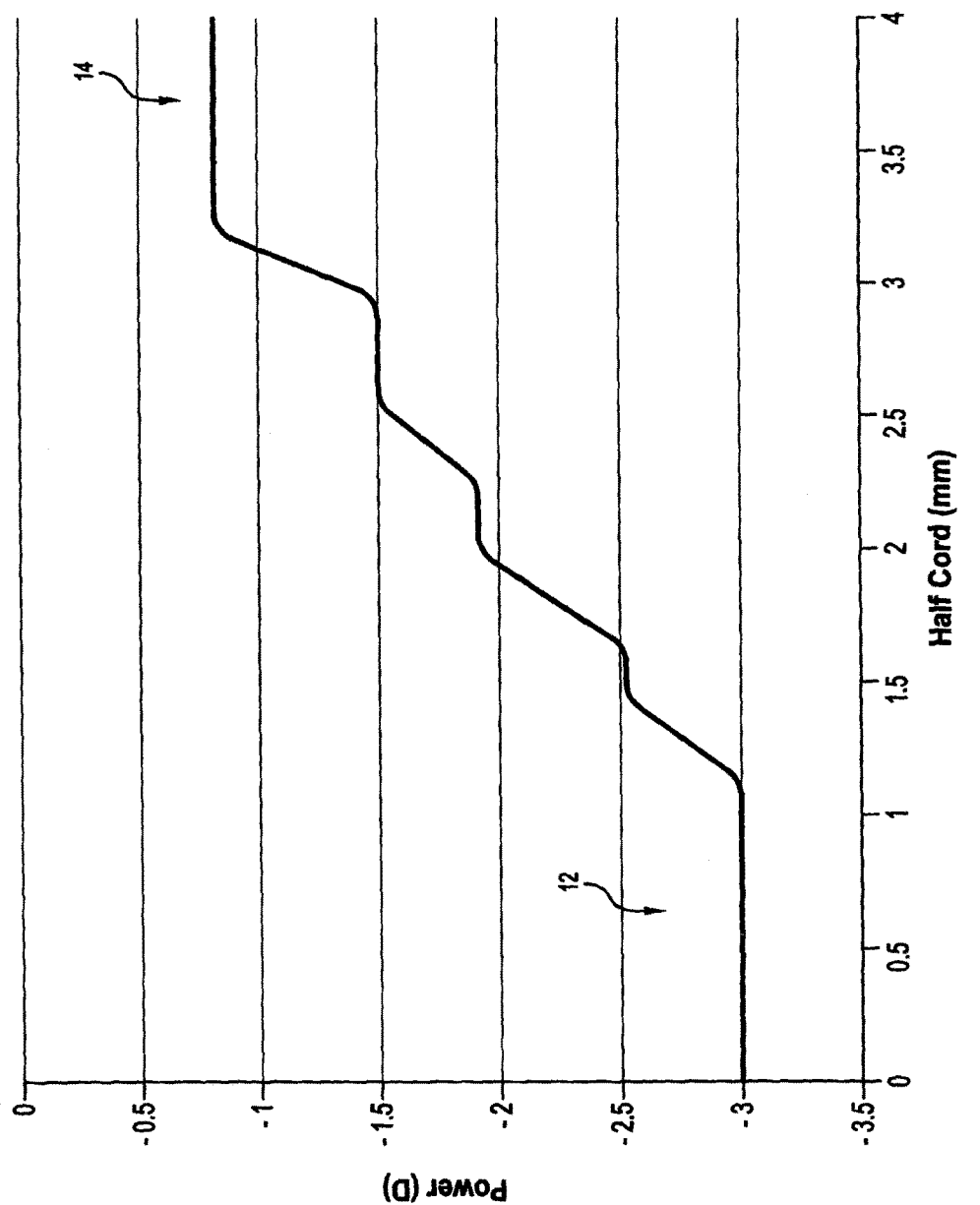

FIGS. 1 to 4 are half-chord diagrams depicting the optical power radially of the optical zone (radius 4 mm) of contact lenses according to some of the disclosed embodiments. In the embodiments of FIGS. 1 and 2, the primary area 12 of the contact lens is located centrally and has a myopia correction power of −3 D, according to the prescription of an individual for whom the contact lens is intended. The primary area thus has a diameter of about 2.1 to 2.2 mm.

Peripherally of this central area is a secondary area 14 in which the optical power transitions to a power more positive than that of the central area resulting in an absolute power of −1.5 D for the FIG. 1 embodiment, and −0.8 D for the FIG. 2 embodiment. The power transitions continuously (that is without discontinuities in magnitude or rate of change), with a number of steps in which the magnitude of the rate of change of the power decreases and then increases.

A primary area may have a primary optical power associated, and a secondary area may have a secondary optical power associated. A power transition may exist between two adjacent areas. For example, the power transition may be between a primary area and a neighbouring secondary area. A power transition is a change in optical power that changes from the optical power of an area to the optical power of an adjacent area. For example, a power transition between a primary area with primary optical power of −3 D and a secondary area with secondary optical power of +1 D may change from −3 D near the primary area in a continuous manner to +1 D near the secondary area.

In the FIG. 1 embodiment, there are two intermediate steps: the first is quite sharp and steep before and after the step, which is itself substantially flat, i.e. no change in power, over a width or depth of about 0.6 mm. Thus a sharp change, for example, means that the magnitude of the change in the magnitude of the rate of change in power with respect to distance across the lens (expressed in dioptres per millimeter squared or $D/mm^2$) may be 20 $D/mm^2$ or greater, and may be up to 100 $D/mm^2$. A change in power before and after a step, may also be denoted as the absolute value of the derivative of the absolute value of the first derivative of power with respect to distance from the optical axis of a lens expressed in dioptres per millimeter squared. A sharp change may also be called a rapid change. The change in power before and after a step may be gradual. A gradual change, for example, means that the magnitude of the change in the magnitude of the rate of change in power with respect to distance across the lens may be 10 $D/mm^2$ or less. The change in power before and after a step may be moderate. A moderate change, for example, lies between a gradual change and a sharp or rapid change. A moderate change, for example, means that the magnitude of the change in the magnitude of the rate of change in power with respect to distance across the lens may be between 10 $D/mm^2$ and 20 $D/mm^2$.

In the FIG. 1 embodiment, the second step is also flat but over a shorter width or depth of about 0.25 mm and is followed by a less rapid increase in optical power to plateau at a radius of about 2.5 mm at the more positive power of −1.5 D.

In the FIG. 2 embodiment, the first step is of less width or depth and the rate of change of the power is substantially similar before and after the two steps, and there is a third step at −1.5 D before the optical power of the secondary area plateaus at −0.3 D at a radius of about 3.3 mm.

Figure 3:
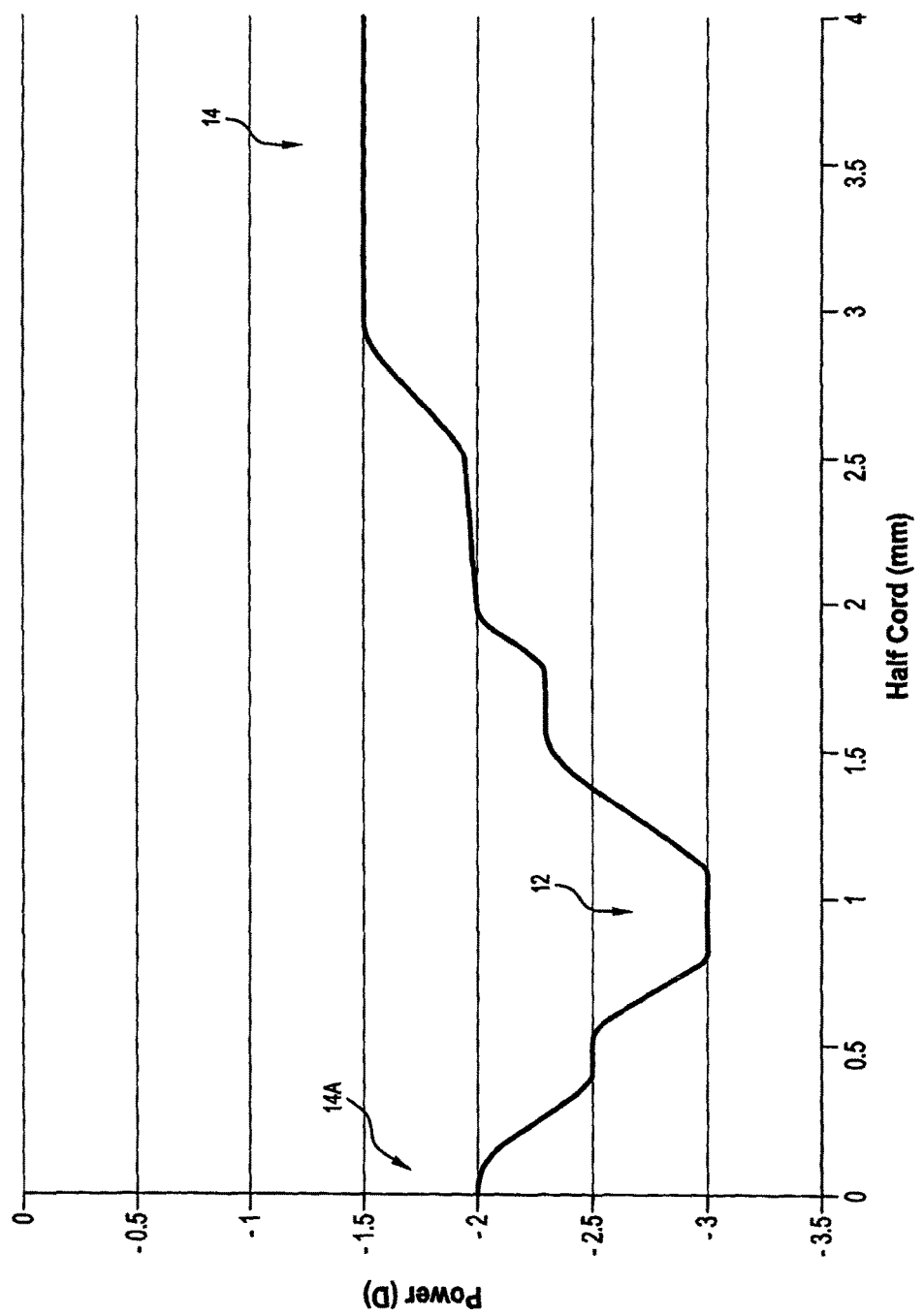

The embodiment of FIG. 3 differs from those of FIGS. 1 and 2 in at least two respects. Firstly, there is a circular secondary area 14A centrally of the optical zone so that the primary area in which the primary optical power is −3 D is reduced to an annulus of about 0.5 mm in width, centred at a radius of 1 mm. This centrally located secondary area 14A has one intermediate step in the power transition en route from the −3 D primary optical power to a central more positive secondary optical power of −2 D. The second difference is that in this case the spacings between the steps both in terms of the width or half-chord distance between steps and in terms of the difference in optical power between steps in the power transition from the primary area to the peripheral secondary area 14 are not substantially uniform as it may be in other embodiments.

Figure 4:
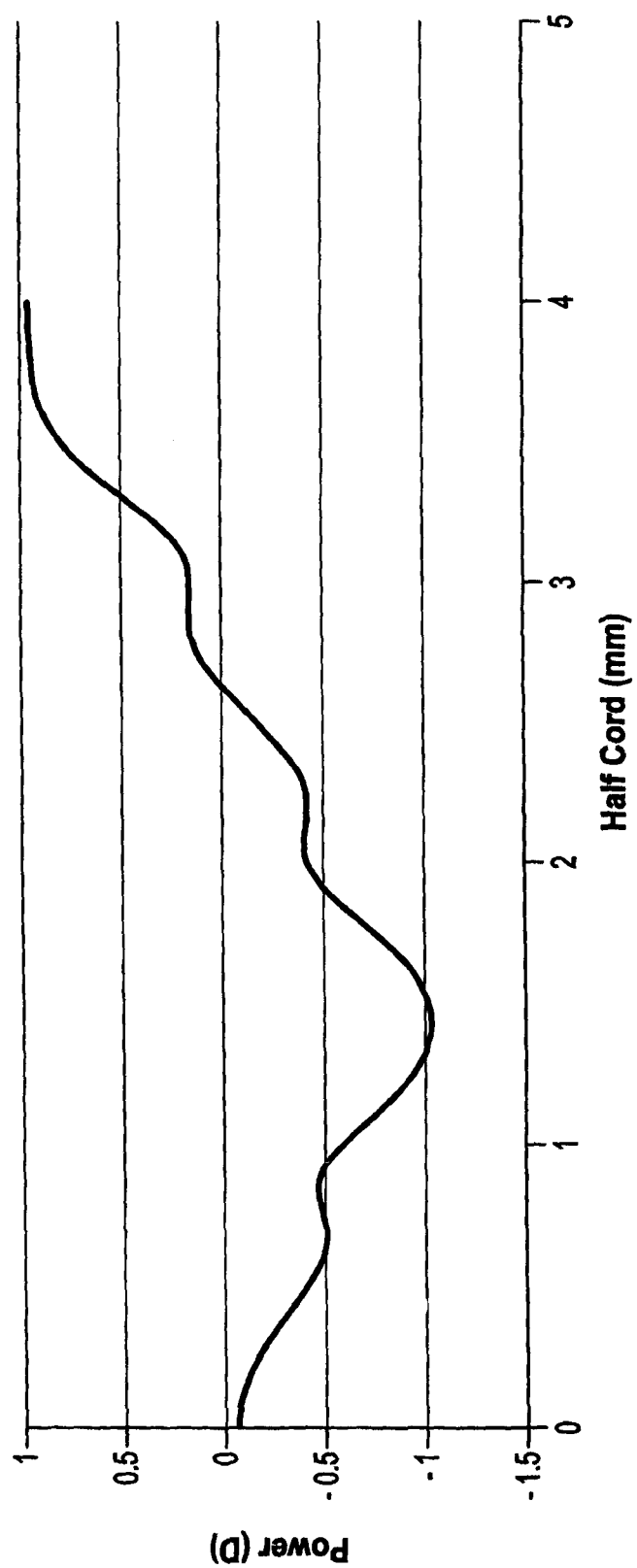

FIG. 4 illustrates an embodiment combining elements of the profiles of the embodiments of FIGS. 1 and 3. Here, a primary area has a distance power of about −1 D, but this is a narrow annular region at a radius of about 1.4 mm.

Figure 5:
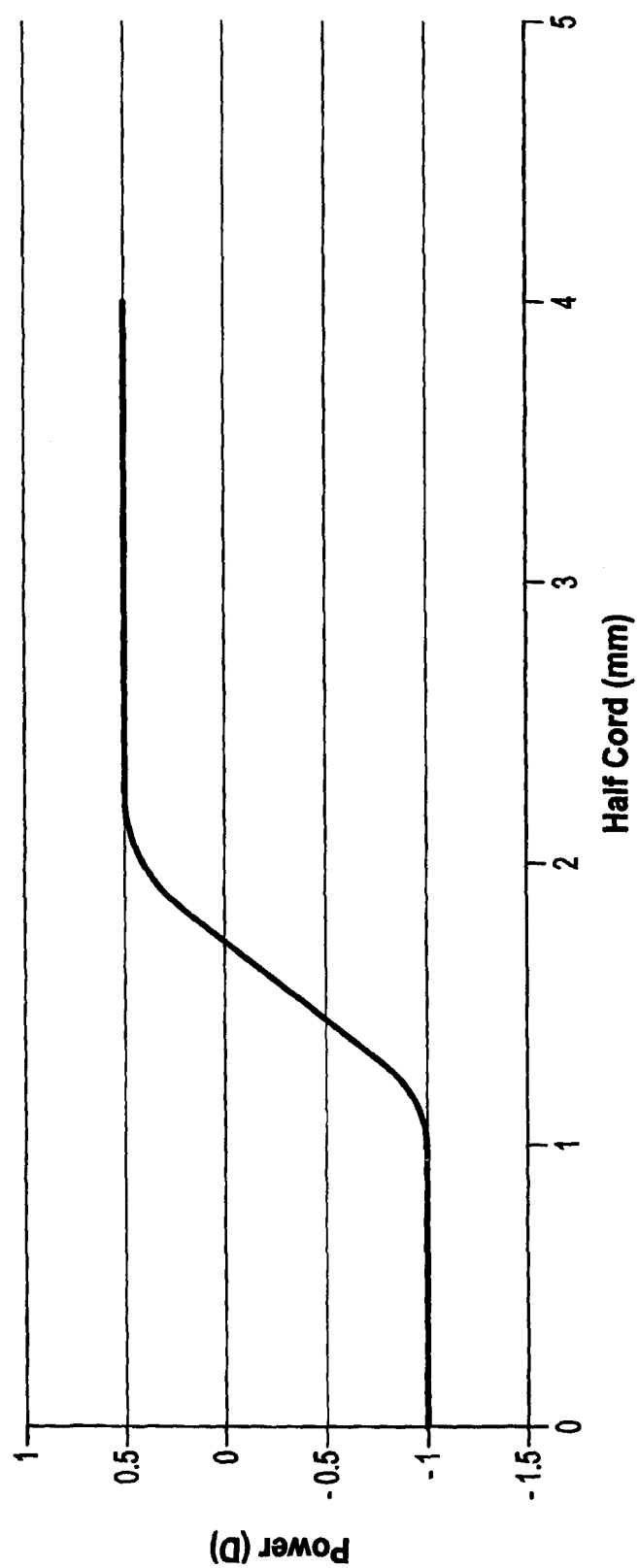
FIG. 5 is a half-chord optical power diagram for an example of a conventional contact lens.

Initial tests were carried out with contact lenses according to FIG. 4 compared to conventional contact lenses of similar distance power in the primary area, but having a smooth, continuous, un-stepped monotonic increase to a peripheral power of 0.5 D. The half-chord power profile for these reference contact lenses is depicted in FIG. 5. The four subjects were selected for exhibiting minimal cylindrical correction (i.e. requiring minimal astigmatic correction)— no more than 0.75 DC—and were asked to assess a variety of elements or aspects of vision performance or visual performance one to four hours after fitting of the lenses. The subjects wore each design bilaterally and these were tested in the same order. Tasks performed by the subjects in assessing the lenses were mainly related to indoor office work. Assessment included vision specific questions including clarity of vision, degree of ghosting, and overall satisfaction.

A power profile of a lens may be based on the design of the lens or may be measured from a manufactured lens. For measurement of a manufactured lens, a number of measurement systems may be used. Some examples of measurement systems include but are not limited to power profiling instruments such as an SHSOphthalmic (Optocraft Gmbh, Germany), a Nimo (Lambda-X, Belgium) and a Phase Focus Lens Profiler (Phase Focus Ltd, UK). Suitably configured, these measurement systems may be used to determine the power profile and the number of steps that are present in the power profile of a lens.

Assessment of vision was by a 1 to 10 numerical rating scale where 1=extremely unclear/blurred and 10=extremely clear/sharp. In distance vision and near vision, the conventional reference lens rated about 6 on average, whereas the exemplary embodiments used rated around 8. In vision overall, it was 5 vs 7.5 respectively. For reporting on the degree of ghosting the scale was 1=no ghosting and 10=severe ghosting. The ghosting at distance and near in the reference design achieved a rating of about 4.5, whereas the rating for the embodiment was 2.5 (i.e. less ghosting).

In overall satisfaction, the score was 5 vs 7.5 with the higher performance score for the illustrated embodiment.

The lens configuration of FIG. 4 resulted in an observable subjective improvement of vision performance or visual performance relative to that of FIG. 5.

Certain embodiments are directed to an ophthalmic lens comprising: an optical zone comprising: at least one primary area with at least one primary optical power; at least one secondary areas comprising: at least one first optical power; wherein at least one of the secondary area is peripheral of the at least one primary area, and the at least one first optical power is more positive than the at least one primary optical power; and wherein there is a first power transition from the at least one primary optical power to the at least one first optical power having at least a first step and a second step, the steps not including the at least one primary area and the at least one secondary area, and wherein for at least one of the first step and second step, the magnitude of the rate of change of the power transitions decreases at the junction before the step and then increases at the junction after the step.

Example 1

Figure 6:
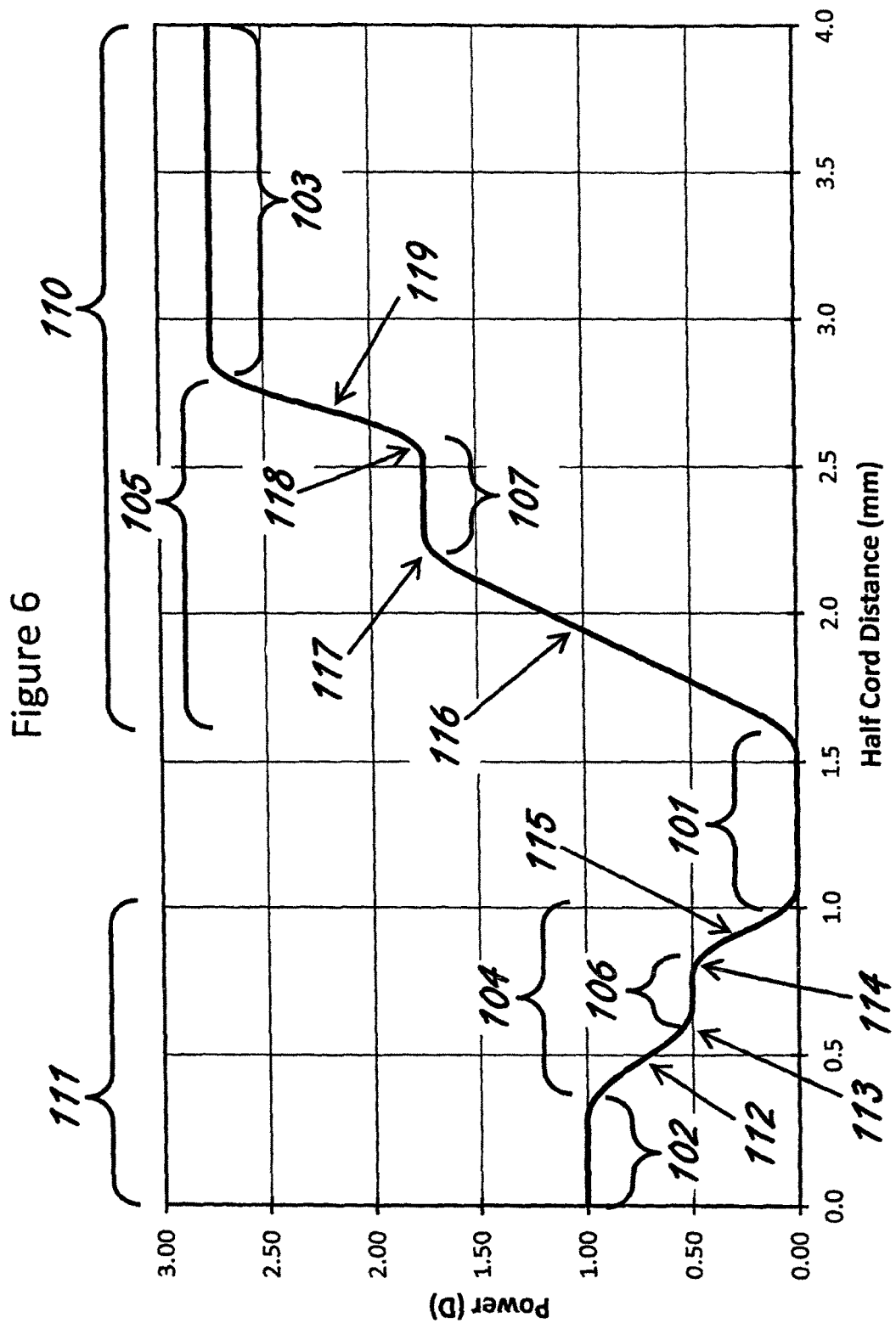
FIG. 6 illustrates an exemplary embodiment of a power profile of an optic zone for a lens.

FIG. 6 illustrates an exemplary embodiment of the power profile of an optic zone for a lens. Power across the optic zone is plotted against the half-chord distance from the centre of the optic zone. The example of FIG. 6 is directed to an ophthalmic lens comprising:
an optic zone comprising:
a primary area 101 having a primary optical power;
a central portion 111;
a first secondary area 102 within the central portion 111 having a first secondary optical power;
a first power transition area 104 having a first power transition from the primary area 101 to the first secondary area 102;
a peripheral portion 110;
a second secondary area 103 within the peripheral portion 110 having a second secondary optical power; and
a second power transition area 105 having a second power transition from the primary area 101 to the second secondary area 103;
wherein the primary optical power is selected according to a prescription for refractive correction, the first secondary optical power is more positive than the primary optical power and the second secondary optical power is more positive than the primary optical power;
wherein the first power transition comprises: at least a first step 106 in the first power transition area 104 in which the rate of change in power, from the first secondary optical power in the first secondary area 102 to the primary optical power in the primary area 101, changes rapidly, that means for example that the magnitude of the change in the magnitude of the rate of change in power with respect to distance across the lens may be 20 D/mm² or greater, at a first junction 113 between a first transition region 112 within the first power transition 104 and the first step 106 followed by a rapid change in the rate of change in power at a second junction 114 between a second transition region 115 within the first power transition 104 and the first step 106, and at least a second step 107 in the second power transition area 105 in which the rate of change in power, from the second secondary optical power in the second secondary area 103 to the primary optical power in the primary area 101, changes rapidly at a third junction 118 between a third transition region 119 of the second power transition 105 and the second step 107 followed by a rapid change in the rate of change in power at a fourth junction 117 between a fourth transition region 116 within the second power transition 105 and the second step 107. In certain embodiments, the magnitude of the rate of change in power with respect to distance across the lens in a transition region may be at least 0.5 D/mm, 1 D/mm, 2 D/mm, 4 D/mm or 8 D/mm.

In the exemplary embodiment of FIG. 6, the optic zone has a diameter of 8 mm (4 mm half-chord). In other embodiments, the optic zone diameter may be at least 3 mm, 5 mm, 6 mm, 7 mm or 8 mm. In the exemplary embodiment of FIG. 6, the primary optical power of the primary area 101 is plano (i.e. 0 D).

In certain embodiments, the primary optical power may be selected according to the prescription for the wearer. In certain embodiments, the primary optical power may comprise a spherical power component. A spherical power component may be used for the correction of myopia, hyperopia, presbyopia or combinations thereof. Spherical power in the primary area may be selected from the range of −20 D to +30 D, −20 D to +20 D, −15 D to +15 D or −10 D to +10 D. In certain embodiments, the primary optical power may further comprise a cylindrical power component. A cylindrical power component may be used for the correction of astigmatism. In certain embodiments, the cylindrical power in the primary area may be selected from the range of −10 D to +10 D or −5 D to +5 D.

In the exemplary embodiment of FIG. 6, the diameter of the centrally located first secondary area is approximately 0.7 mm (i.e. half-chord distance of approximately 0.35) and the width (half-chord distance) of the second secondary area is approximately 1.1 mm. In certain embodiments, the width of a secondary area may be between 0 mm and 2 mm, 0.1 mm and 1.75 mm or 0.2 mm and 1.5 mm.

In the exemplary embodiment of FIG. 6, the width (half-chord distance) of the primary area 101 is approximately 0.6 mm.

In certain embodiments, the width of a primary area may be between 0.2 mm and 2 mm, 0.3 mm and 1.75 mm or 0.4 mm and 1.5 mm.

In the exemplary embodiment of FIG. 6, the power of the first secondary area is 1 D more positive than the primary optical power and the second secondary optical power is 2.75 D greater than the optical power of the primary area.

In certain embodiments, the power of a secondary area may be up to 5 D, 4 D or 3 D more positive than a power of a primary area. In certain embodiments, the power of two or more secondary areas may be the same, substantially the same or different.

In the exemplary embodiment of FIG. 6, the width of the first step 106 is approximately 0.2 mm and the width of the second step 107 is approximately 0.4 mm.

In certain embodiments, the width of a step may be between 0 mm and 1.5 mm, 0.1 mm and 1.25 mm, 0.1 mm and 1 mm or 0.15 mm and 1 mm.

In the exemplary embodiment of FIG. 6, the power of the first step 106 is approximately 0.5 D more positive than the optical power of the primary area 101 and the power of the second step 107 is approximately 1.75 D greater than the optical power of the primary area 101. In the exemplary embodiment of FIG. 6, the power of the first step 106 is approximately 0.5 D less positive than the optical power of the first secondary area 102 and the power of the second step 107 is approximately 1 D less than the optical power of the second secondary area 103.

In certain embodiments, the power of a step may be up to 5 D, 4 D or 3 D more positive than a power of a primary area. In certain embodiments, the power of a step may be up to 5 D, 4 D or 3 D less positive or more negative than a power of a secondary area. In certain embodiments, the power of two or more steps may be the same, substantially the same or different.

In the exemplary embodiment of FIG. 6, changes in the rate of change in optical power at junctions 113 and 114 that forms the first step 106 and changes in the rate of change in optical power at junctions 117 and 118 that forms the second step 107 are rapid.

In certain embodiments, a change in the rate of change in optical powers may be considered "rapid" when the change in rate of change occurs over a junction width of less than 0.3 mm, 0.25 mm, 0.2 mm or 0.15 mm. How rapid a change in the rate of change in optical power may occur may be constrained by lens manufacturing processes.

Example 2

Figure 10:
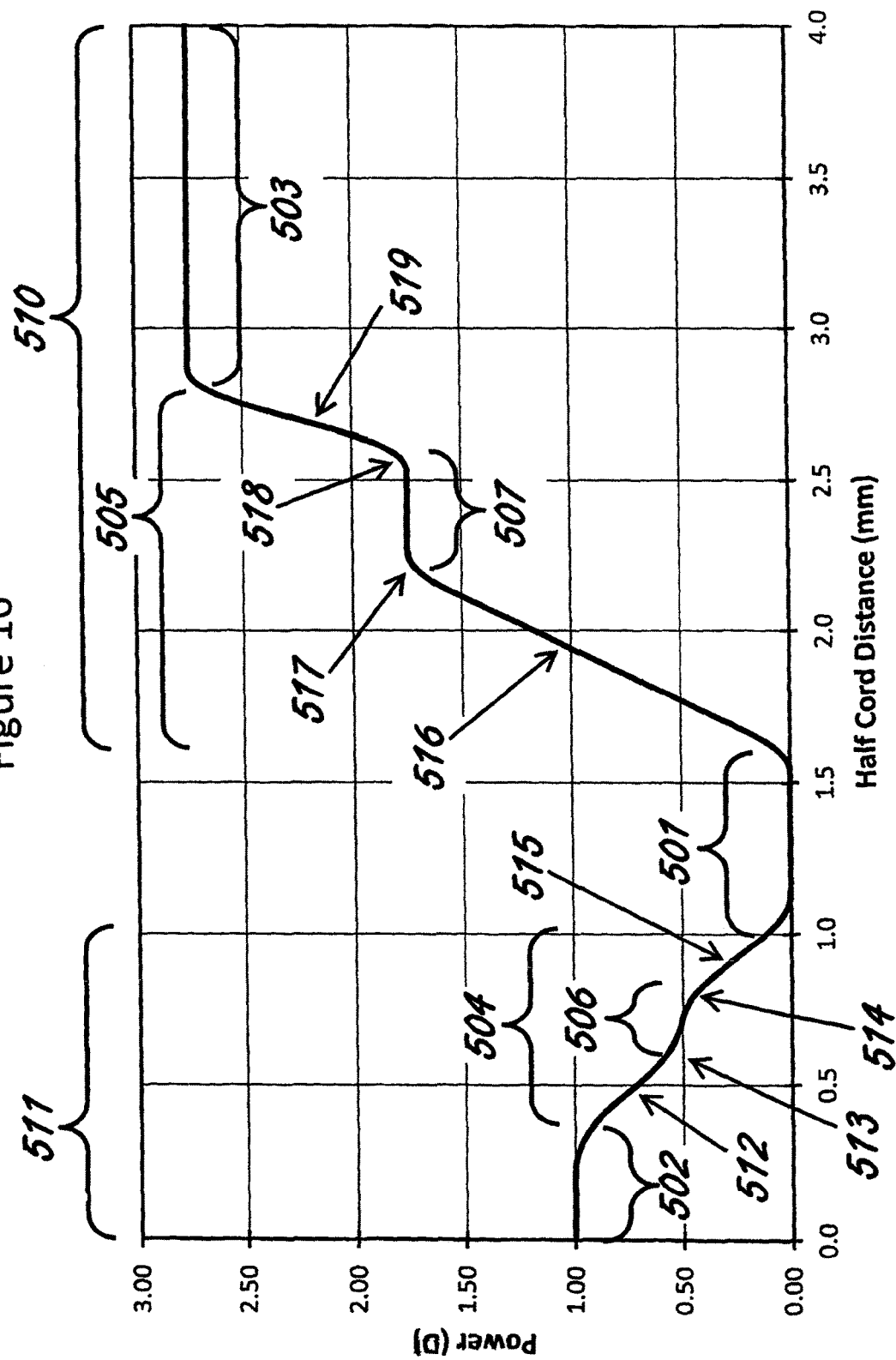
FIG. 10 illustrates an exemplary embodiment of a power profile of an optic zone for a lens.

FIG. 10 illustrates an exemplary embodiment of the power profile of an optic zone for a lens. Power across the optic zone is plotted against the half-chord distance from the centre of the optic zone. The example of FIG. 10 is directed to an ophthalmic lens comprising:
an optic zone comprising:
a primary area 501 having a primary optical power;
a central portion 511;
a first secondary area 502 within the central portion 511 having a first secondary optical power;
a first power transition area 504 having a first power transition from the primary area 501 to the first secondary area 502;
a peripheral portion 510;
a second secondary area 503 within the peripheral portion 510 having a second secondary optical power; and
a second power transition area 505 having a second power transition from the primary area 501 to the second secondary area 503;
wherein the primary optical power is selected according to a prescription for refractive correction, the first secondary optical power is more positive than the primary optical power and the second secondary optical power is more positive than the primary optical power;
wherein the first power transition comprises: at least a first step 506 in the first power transition area 504 in which the rate of change in power, from the first secondary optical power in the first secondary area 502 to the primary optical power in the primary area 501, changes rapidly at a first junction 513 between a first transition region 512 within the first power transition 504 and the first step 506 followed by a rapid change in the rate of change in power at a second junction 514 between a second transition region 515 within the first power transition 504 and the first step 506, and
at least a second step 507 in the second power transition area 505 in which the rate of change in power, from the second secondary optical power in the second secondary area 503 to the primary optical power in the primary area 501, changes rapidly at a third junction 518 between a third transition region 519 of the second power transition 505 and the second step 507 followed by a rapid change in the rate of change in power at a fourth junction 517 between a fourth transition region 516 within the second power transition 505 and the second step 507.

Figure 11:
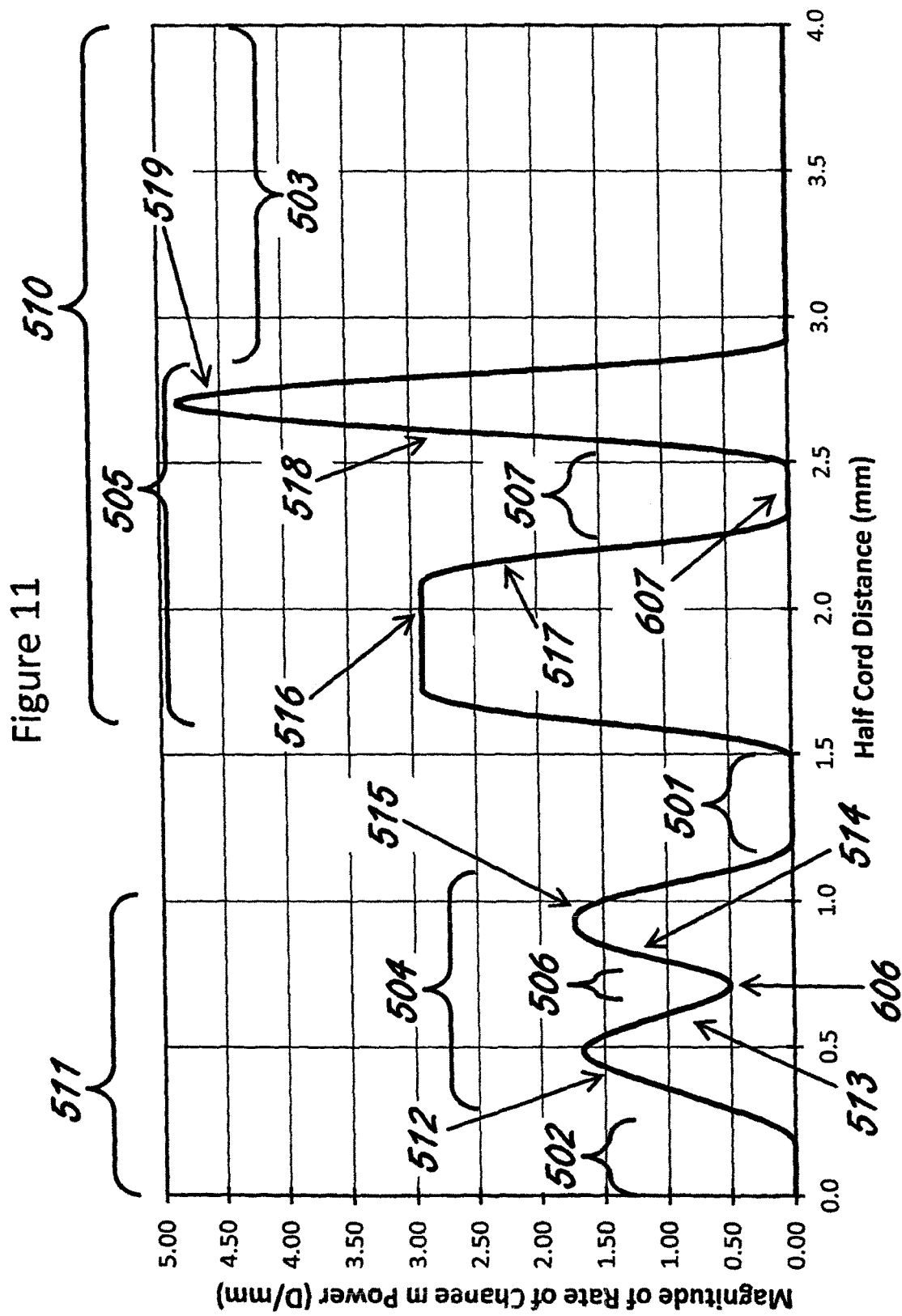
FIG. 11 illustrates the magnitude of the rate of change of a power profile of an optic zone for the exemplary embodiment of FIG. 10.

FIG. 11 is a plot of magnitude of the rate of change in power across the optical zone of the exemplary embodiment shown in FIG. 10. The primary area 501, inner and outer portions 511 and 510, secondary areas 502 and 503, power transitions 504 and 505 and first and second steps 506 and 507 of the exemplary embodiment are also shown in FIG. 11. The magnitude of the rate of change in power is the absolute value of the rate of change in power, i.e. the absolute value of the slope of the power along the optic zone. This can be described by equation 1:

$$R = \left| \frac{dP}{dX} \right| \qquad (1)$$

in which
X is a half-chord distance, and
P is the power at half-chord distance X
R is the magnitude of the rate of change in power P at half-chord distance X
The unit for magnitude of the rate of change in power is D/mm (dioptres per millimeter).

The units for the magnitude of the change in the magnitude of the rate of change in power (that is, the absolute value of the derivative of R with respect to X) is D/mm$^2$ (dioptres per millimeter squared).

In FIG. 10, the first step 506 has a gradual change in the rate of change in power at the first junction 513 between the first transition region 512 and the first step 506 and also a gradual change in the rate of change in power at the second junction 514 between the second transition region 515 and the first step 506. In FIG. 11, magnitude of the rate of change in power approaching the first step 506 from the first secondary area 502 and then departing the first step towards the primary area 501 can be seen as a decrease in the magnitude of the rate of change in power at the first transition region 512 and first junction 513 followed by an increase in the magnitude of the rate of change in power at the second junction 514 and second transition region 515. In the exemplary embodiment, the change in the magnitude of the rate of change in power at junctions 513 and 514 are gradual and is approximately 7 D/mm$^2$ for the first junction 513 and 9 D/mm$^2$ for the second junction 514.

In FIG. 10, the second step 507 has a rapid change in the magnitude of the rate of change in power at the fourth junction 517 between the fourth transition region 516 and the second step 507 and a more rapid change in the magnitude of the rate of change in power at the third junction 518 between the third transition region 519 and the second step 507. In FIG. 11, magnitude of the rate of change in power approaching the second step 507 from the second secondary area 503 and then departing the first step towards the primary area 501 can be seen as a decrease in the magnitude of the rate of change in power at the third transition region 519 and third junction 518 followed by an increase in the magnitude of the rate of change in power at the fourth junction 517 and fourth transition region 516. In the exemplary embodiment, the magnitude of the change in the magnitude of the rate of change in power at junctions 517 and 518 are rapid to very rapid and is approximately 20 D/mm$^2$ for the fourth junction 517 and 35 D/mm$^2$ for the third junction 518.

In certain embodiments, the change in the magnitude of the rate of change in power at a junction may be very rapid and may be up to 100 D/mm$^2$.

Thus, in the exemplary embodiment, for both first step and second step, the magnitude of the rate of change of power decreases and then increases. That is, there is a point, or a width, where there is a local minimum in the magnitude of the rate of change in power. In FIG. 11, the minimum corresponding to the first step 506 is at the point 606 and the minimum corresponding to the second step 507 is along the width 607.

In certain embodiments, a power transition between a secondary area and a primary area has a step when the magnitude of the rate of change in power along the power transition decreases and then increases. In certain embodiments, the decrease followed by increase in the magnitude of the rate of change in power along the power transition may occur one or more times (i.e. the power transition has one or more steps). In certain embodiments, a minimum in the magnitude of the rate of change in power along a power transition is one of a point, substantially a point and a width. In certain embodiments, a minimum in the magnitude of the rate of change in power along a power transition has a width of between 0 and 1 mm, 0 and 0.75 mm or 0 and 0.5 mm.

In certain embodiments, the magnitude of the rate of change in power at a minimum of the magnitude of the rate of change in power of a step may be between 0 D/mm to 0.75 D/mm, 0 D/mm to 0.6 D/mm or 0 D/mm to 0.5 D/mm or 0 D/mm to 1 D/mm.

In certain embodiments, the rate of change of the magnitude of the rate of change in power at a junction between a transition region and a step may be between 1 D/mm$^2$ to 100 D/mm$^2$ or 5 D/mm$^2$ to 50 D/mm$^2$.

Example 3

Figure 7:
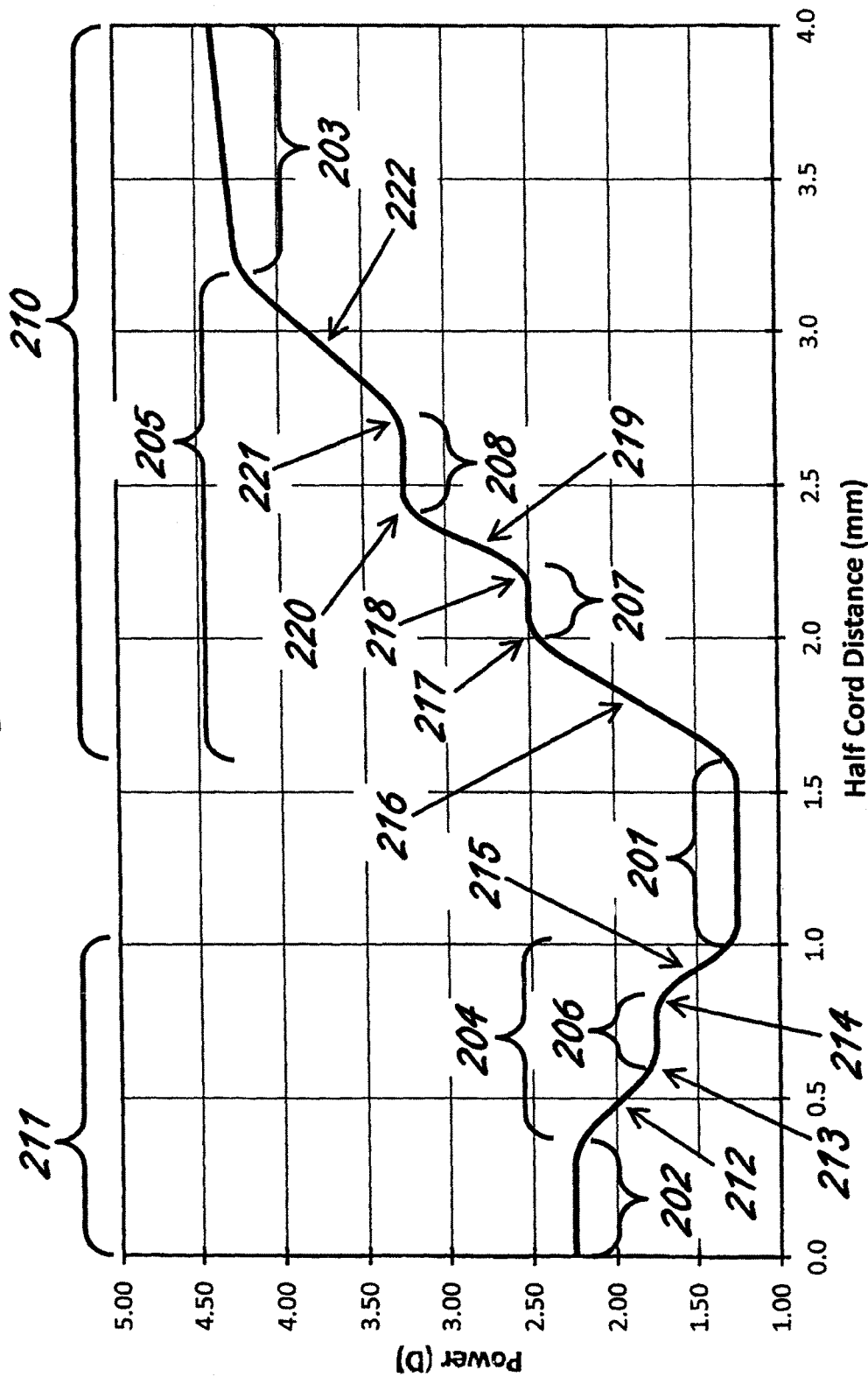
FIG. 7 illustrates an exemplary embodiment of a power profile of an optic zone for a lens.

FIG. 7 illustrates an exemplary embodiment of the power profile of an optic zone for a lens. Power across the optic zone is plotted against the half-chord distance from the centre of the optic zone. The example of FIG. 7 is directed to an ophthalmic lens comprising:
an optic zone comprising:
a primary area 201 having a primary optical power;
a central portion 211;
a first secondary area 202 within the central portion 211 having a first secondary optical power;
a first power transition area 204 having a first power transition from the primary area 201 to the first secondary area 202;
a peripheral portion 210;
a second secondary area 203 within the peripheral portion 210 having a second secondary optical power; and
a second power transition area 205 having a second power transition from the primary area 201 to the second secondary area 203;
wherein the primary optical power is selected according to a prescription for refractive correction, the first secondary optical power is more positive than the primary optical power and the second secondary optical power is more positive than the primary optical power;
wherein the first power transition comprises: at least a first step 206 in the first power transition area 204 in which the rate of change in power, from the first secondary optical power in the first secondary area 202 to the primary optical power in the primary area 201, changes rapidly at a first junction 213 between a first transition region 212 within the first power transition 204 and the first step 206 followed by a rapid change in the rate of change in power at a second junction 214 between a second transition region 215 within the first power transition 204 and the first step 206, and
at least a second step 207 and a third step 208,
wherein the second step 207 lies within the second power transition area 205 in which the rate of change in power, from the second secondary optical power in the second secondary area 203 to the primary optical power in the primary area 201, changes rapidly at a third junction 218 between a third transition region 219 within the second power transition 205 and the second step 207 followed by a rapid change in the rate of change in power at a fourth junction 217 between a fourth transition region 216 within the second power transition 205 and the second step 207, and the third step 208 lies within the second power transition area 205 in which the rate of change in power, from the second secondary optical power in the second secondary area 203 to the primary optical power in the primary area 201, changes rapidly at a fifth junction 221 between a fifth transition region 221 within the second power transition 205 and the third step 208 followed by a rapid change in the rate of change in power at a sixth junction 220 between a third transition region 219 within the second power transition 205 and the third step 208.

In the exemplary embodiment of FIG. 7, the primary optical power of the primary area 201 is 1.25 D.

In certain embodiments, the primary optical power may be selected according to the prescription for the wearer. Such prescription may be provided for the correction of one or more of myopia, hyperopia, astigmatism and presbyopia.

In the exemplary embodiment of FIG. 7, the diameter of the first secondary area is approximately 0.7 mm (i.e. half-chord distance of approximately 0.35 mm) and the width (half-chord distance) of the second secondary area is approximately 0.8 mm.

In certain embodiments, the width of a secondary area may be between 0 mm and 2 mm, 0.1 mm and 1.75 mm or 0.2 mm and 1.5 mm.

In the exemplary embodiment of FIG. 7, the power of the first secondary area 202 is 1 D more positive than the primary optical power and the second secondary optical power is more than 3.25 D greater than the optical power of the primary area 201. In exemplary embodiment of FIG. 7, the second secondary area 203 has a progression in optical power beginning from approximately 4.25 D then progressively increasing in positive power towards the periphery.

Such peripheral progressive increase in power may reduce eye growth and/or reduce myopia progression.

In certain embodiments, the power of a secondary area may be constant, substantially constant, progressively increasing, progressively decreasing, modulated (i.e. undulating along its power profile), possess an aberration profile (e.g. spherical aberration) or combinations thereof.

In the exemplary embodiment of FIG. 7, the inner or central portion 211 has a step 206 in the first power transition 204 from the first secondary area 202 to the primary area 201 and the outer or peripheral portion 210 has two steps 207 and 208 in the second power transition 205 from the second secondary area 203 to the primary area 201.

In certain embodiments, the number of steps within either an inner or central portion or an outer or peripheral portion may be equal to or greater than 1, 2, 3, 4 or 5. In certain embodiments, the number of steps within an inner portion, meaning for example the central portion, may be equal to or greater than 1, 2, 3 or 4. In certain embodiments, the number of steps within an outer portion, meaning for example the portion outside the central or inner portion, may be equal to or greater than 1, 2, 3, 4, 5 or 6. In certain embodiments, the number of steps within either an inner or central portion or an outer or peripheral portion may be between 1 and 6, 1 and 5, 2 and 6, 2 and 5 or 2 and 4. In certain embodiments, the number of steps in an inner portion may be equal to the number of steps in an outer portion. In certain embodiments, the number of steps in an inner portion and the number of steps in an outer portion may be unequal.

In the exemplary embodiment of FIG. 7, the first power transition 204 between the first secondary area 202 and the primary area 201 has a step 206 and the second power transition 205 from the second secondary area 203 to the primary area 201 has two steps 207 and 208. In certain embodiments, the number of steps within a power transition may be equal to or greater than 1, 2, 3, 4 or 5.

In certain embodiments, the number of steps within a power transition adjacent to or joining a secondary area may be equal to or greater than 1, 2, 3, 4, 5 or 6. In certain embodiments, the number of steps within a power transition adjacent to or joining a centrally located secondary area may be equal to or greater than 1, 2, 3 or 4. In certain embodiments, the number of steps in two or more power transitions may be equal. In certain embodiments, the number of steps in two or more power transitions may be unequal.

Example 4

Figure 8:
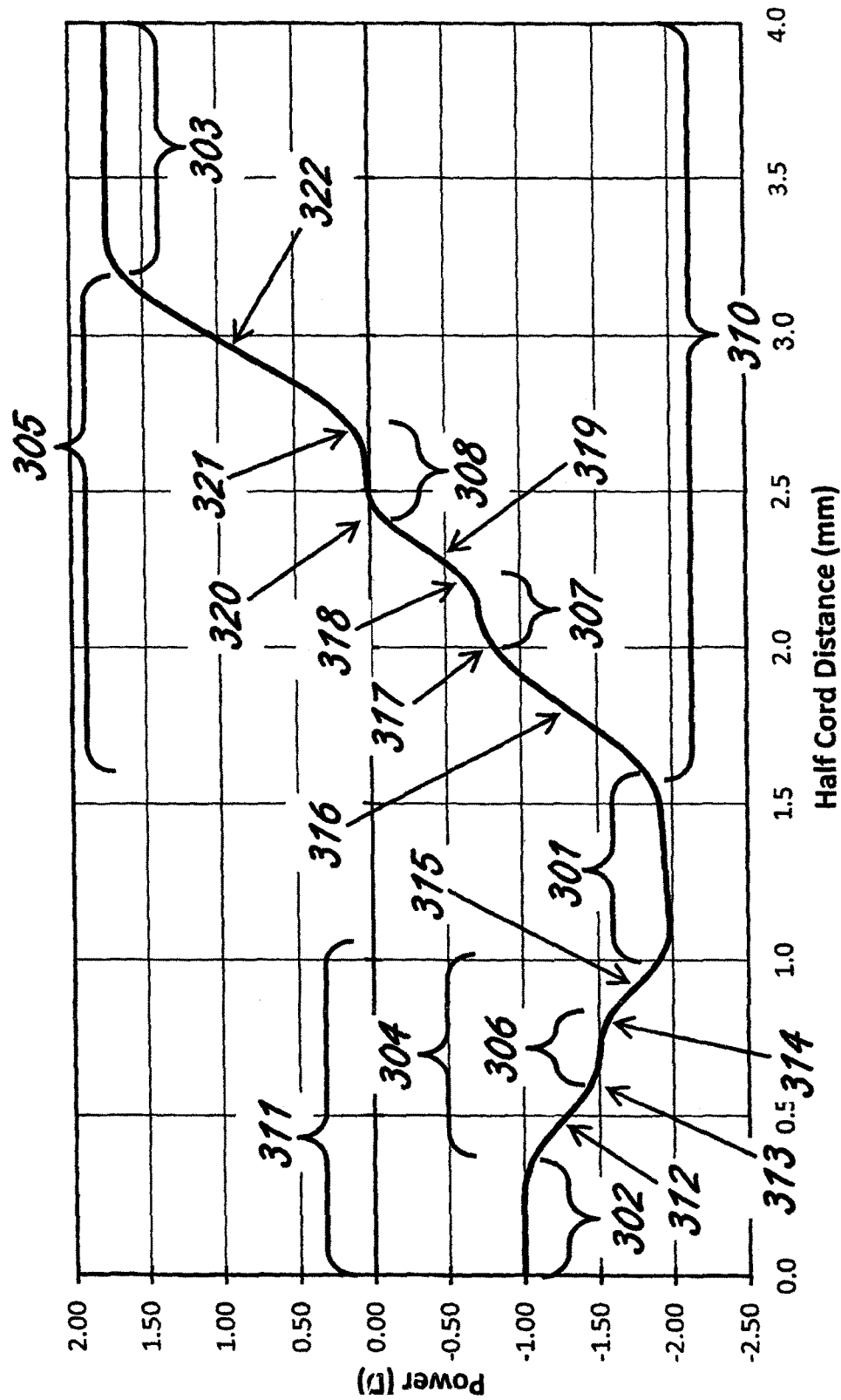
FIG. 8 illustrates an exemplary embodiment of a power profile of an optic zone for a lens.

FIG. 8 illustrates an exemplary embodiment of the power profile of an optic zone for a lens. The example of FIG. 8 is directed to an ophthalmic lens comprising:
an optic zone comprising:
a primary area 301 having a primary optical power;
a central portion 311;
a first secondary area 302 within the central portion 311 having a first secondary optical power; a first power transition area 304 having a first power transition from the primary area 301 to the first secondary area 302;
a peripheral portion 310;
a second secondary area 303 within the peripheral portion 310 having a second secondary optical power; and
a second power transition area 305 having a second power transition from the primary area 301 to the second secondary area 303;
wherein the primary optical power is selected according to a prescription for refractive correction, the first secondary optical power is more positive than the primary optical power and the second secondary optical power is more positive than the primary optical power;
wherein the first power transition comprises: at least a first step 306 in the first power transition area 304 in which the rate of change in power, from the first secondary optical power in the first secondary area 302 to the primary optical power in the primary area 301, changes at a first junction 313 between a first transition region 312 within the first power transition 304 and the first step 306 followed by a change in the rate of change in power at a second junction 314 between a second transition region 315 within the first power transition 304 and the first step 306, and
at least a second step 307 and a third step 308,
wherein the second step 307 lies within the second power transition area 305 in which the rate of change in power, from the second secondary optical power in the second secondary area 303 to the primary optical power in the primary area 301, changes at a third junction 318 between a third transition region 319 within the second power transition 305 and the second step 307 followed by a change in the rate of change in power at a fourth junction 317 between a fourth transition region 316 within the second power transition 305 and the second step 307, and the third step 308 lies within the second power transition area 305 in which the rate of change in power, from the second secondary optical power in the second secondary area 303 to the primary optical power in the primary area 301, changes at a fifth junction 321 between a fifth transition region 321 within the second power transition 305 and the third step 308 followed by a change in the rate of change in power at a sixth junction 320 between the third transition region 319 within the second power transition 305 and the third step 308.

In the exemplary embodiment of FIG. 8, the power of the primary area 301 is approximately −2 D and has a progression in optical power progressively increasing in positive power towards the periphery. Such peripheral progressive increase in power may result in effective or improved visual performance or vision performance in one or more aspects of visual performance or vision performance. For example, spherical aberration may be included in the primary area to correct, reduce or manipulate aberration of the eye and ophthalmic lens combined. Such an exemplary inclusion of spherical aberration may improve clarity of vision, contrast, contrast sensitivity, visual acuity, and overall quality of vision or combinations thereof.

In certain embodiments, the power of a primary area may be constant, substantially constant, progressively increasing, progressively decreasing, modulated (i.e. undulating along its power profile), possess an aberration profile (e.g. spherical aberration) or combinations thereof.

In the exemplary embodiment of FIG. 8, the powers of the first step 306, second step 307 and third step 308 are not constant within the steps.

In certain embodiments, the power profile within a step may be constant, or substantially constant, or progressively changing. In certain embodiments in which the power of a step is progressively changing, the change in power across the width of the step may be between 0 and 0.2 D, 0 and 0.15 D or 0 and 0.1 D. In certain embodiments in which two or more steps have progressively changing power profiles, the rate of change of the power profiles between the two or more steps may be equal or unequal.

In the exemplary embodiment of FIG. 8, the power profile along the first power transition 304 and the second power transition 305 are monotonic.

Monotonic means that where a power transition decreases from one area to another area (for example, between a first secondary area and a primary area), the power profile is either decreasing or constant or substantially decreasing or substantially constant along the power transition including steps within the power transition. Conversely, where a power transition increases from one area to another area (for example, from a primary area to a second secondary area), monotonic means the power profile is either increasing or constant or substantially increasing or substantially constant along the power transition including steps within the power transition. In certain embodiments, a power transition will have a monotonic power profile.

In the exemplary embodiment of FIG. 8, changes in the rate of change in optical power at junctions 313 and 314 that forms the first step 306 and changes in the rate of change in optical power at junctions 317 and 318 that forms the second step 307 are less rapid and/or more gradual.

In certain embodiments, a change in the rate of change in optical powers may be considered "gradual" when the change in rate of change occurs over a junction width of between 0.15 and 1 mm, 0.25 and 0.75 mm or 0.3 and 0.5 mm.

Example 5

Figure 9:
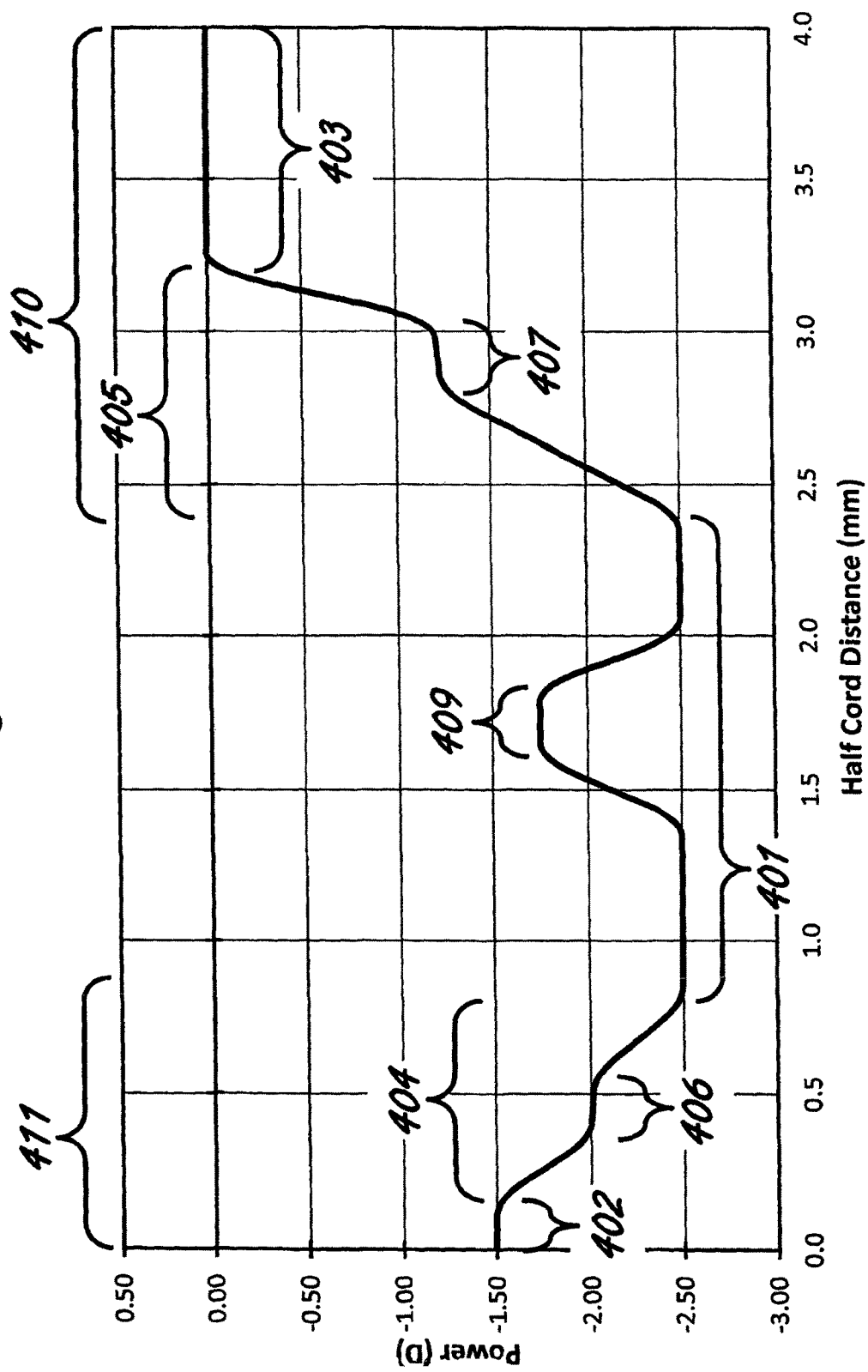
FIG. 9 illustrates an exemplary embodiment of a power profile of an optic zone for a lens.

FIG. 9 illustrates an exemplary embodiment of the power profile of an optic zone for a lens. The example of FIG. 9 is directed to an ophthalmic lens comprising:
an optic zone comprising:
a primary area 401 having a primary optical power;
a central portion 411;
a first secondary area 402 within the central portion 411 having a first secondary optical power;
a first power transition area 404 having a first power transition from the primary area 401 to the first secondary area 402;
a peripheral portion 410;
a second secondary area 403 within the peripheral portion 410 having a second secondary optical power; and
a second power transition area 405 having a second power transition from the primary area 401 to the second secondary area 403;
wherein the first secondary optical power is more positive than the primary optical power and the second secondary optical power is more positive than the primary optical power;
wherein the first power transition comprises: at least a first step 406 in the first power transition area 404, and
at least a second step 407 within the second power transition area 405, and
the primary area 401 comprises an optical region 409 with a different optical power than the primary area.

In the exemplary embodiment of FIG. 9, the power of the primary area 401 is approximately −2.5 D and has an annular optical region 409 with an optical power of approximately 0.75 D more positive than the primary power. Such an optical region may provide improved near vision for the correction of presbyopia and/or the reduction of eye growth and/or reduction in myopia progression.

In certain embodiments, a primary area may have one or more optical regions with optical power different or substantially different from the primary area. In certain embodiments, a primary area may have one or more optical regions with optical power more positive or substantially more positive than the primary area. In certain embodiments, in which a primary area may have two or more optical regions, the optical power of the two or more optical regions within the primary area may be equal, substantially equal or different.

Certain embodiments are direct to the use of a lens with the exception of such uses that comprise or encompass an invasive step representing a substantial physical intervention on the body of a human or an animal which requires professional medical expertise to be carried out and which entail a substantial health risk even when carried out with the required professional care and expertise, for example uses comprising the step of introducing the lens into and/or onto a human or animal eye, invasively changing the optical characteristics and/or permanently deforming of a lens comprised by a human or animal eye or exchanging at least a part of a lens comprised by a human or animal eye.

Other Exemplary Non-Limiting Embodiments

Further advantages of the claimed subject matter will become apparent from the following exemplary embodiments. CL Example A1

An ophthalmic lens comprising: an optical zone with a primary area having an optical power and one or more secondary areas;
wherein at least one of the one or more of the secondary areas is located peripheral to the primary area;
wherein the one or more secondary areas has an optical power that is more positive relative to the optical power of the primary area;
wherein between the primary area and at least one or the one or more of the secondary areas, the optical power progressively transitions between the more negative and more positive powers with at least one step that does not include the primary and the at least one of the one or more secondary areas in which the magnitude of the rate of change of the power decreases and then increases.

Example A2

An ophthalmic lens comprising:
an optical zone comprising:
at least one primary area with at least one primary optical power;
a first secondary area with a first optical power; and
a second secondary area with a second optical power;
wherein at least one of the first secondary area and the second secondary area is peripheral of the at least one primary area, and the first and second optical powers are more positive than the at least one primary optical power; and
wherein between adjacent primary area and secondary areas, there is a transition in power from the primary optical power to the secondary optical power of the adjacent secondary area with at least one step that does not include the primary and secondary powers in the primary and secondary areas in which the magnitude of the rate of change of the transition in power decreases and then increases.

Example A3

An ophthalmic lens comprising:
an optical zone comprising:
at least one primary area with at least one primary optical power;
at least two secondary areas comprising: a first secondary area with a first optical power and a second secondary area with a second optical power;
wherein at least one of the first secondary area and the second secondary area is peripheral of the at least one primary area, and the first and second optical powers are more positive than the at least one primary optical power; wherein there is a transition in power from the at least one primary optical power to at least one of the first optical power and the second optical power with at least one step that does not include the at least one primary optical power and the first and secondary optical in which the magnitude of the rate of change of the transition in power decreases rapidly and then increases rapidly when the at least one primary area is adjacent to one of the first secondary area and the second secondary area.

Example A4

An ophthalmic lens for correcting a refractive error of an eye and for controlling eye growth, including an optical zone with a primary area having an optical power and one or more secondary areas, including at least one peripherally of the primary area, having an optical power that is more positive relative to the optical power of the primary area, wherein between the primary area and the secondary area(s), the optical power progressively transitions between the more negative and more positive powers with at least one step that does not include the primary and secondary area(s) in which the magnitude of the rate of change of the power decreases and then increases by amounts and over a distance sufficient to improve vision performance or visual performance experienced with the lens.

A5

The ophthalmic lens of one or more of Examples A1 to A3, wherein the lens is for correcting refractive error of an eye.

A6

The ophthalmic lens of one or more of Examples A1 to A3, wherein the lens is for correcting refractive error of an eye and for controlling eye growth.

A7

The ophthalmic lens of one or more of Examples A1 to A6, wherein the secondary optical power is more positive than the primary optical power by between 0.5 D to 3.5 D, 0.75 D to 2.5 D or 1 D to 2.5 D.

A8

The ophthalmic lens of one or more of Examples A1 to Ax6 wherein the secondary optical power is more positive than the primary optical power by at least 0.5 D, 0.75 D, 1 D, 2 D, 2.5 D, 3 D or 3.5 D.

A9

The ophthalmic lens of one or more of Examples A1 to A8, wherein the width of the primary area is about 0.2 mm, 0.5 mm, 1 mm, 2 mm, 3 mm, 4 mm or 5 mm.

A10

The ophthalmic lens of one or more of Examples A1 to A8, wherein the width of the primary area is between 0.2 mm to 5 mm, 0.5 to 1 mm, 0.5 mm to 2 mm, 0.5 mm to 3 mm, 1 mm to 4 mm or 2 mm to 4 mm.

A11

The ophthalmic lens of one or more of Examples A1 to A10, wherein the width of a central secondary area is between 0 mm to 3 mm, 0.5 mm to 3 mm, 1 mm to 2.5 mm or 2 mm to 2.5 mm.

A12

The ophthalmic lens of one or more of Examples A1 to A11, wherein the width of at least one of the steps is approximately 0.1 mm, 0.2 mm or 0.3 mm.

A13

The ophthalmic lens of one or more of Examples A1 to A11, wherein the width of at least two of the steps is approximately 0.1 mm, 0.2 mm or 0.3 mm.

A14

The ophthalmic lens of one or more of Examples A1 to A11, wherein the width of at least three of the steps is approximately 0.1 mm, 0.2 mm or 0.3 mm.

A15

The ophthalmic lens of one or more of Examples A1 to A11, wherein the width of at least four of the steps is approximately 0.1 mm, 0.2 mm or 0.3 mm.

A16

The ophthalmic lens of one or more of Examples A1 to A11, wherein the width of at least one of the steps is about 0.1 mm, 0.2 mm or 0.3 mm.

A17

The ophthalmic lens of one or more of Examples A1 to A11, wherein the width of at least two of the steps is about 0.1 mm, 0.2 mm or 0.3 mm.

A18

The ophthalmic lens of one or more of Examples A1 to A11, wherein the width of at least three of the steps is about 0.1 mm, 0.2 mm or 0.3 mm.

A19

The ophthalmic lens of one or more of Examples A1 to A11, wherein the width of at least four of the steps is about 0.1 mm, 0.2 mm or 0.3 mm.

A20

The ophthalmic lens of one or more of Examples A1 to A19, wherein the rate of change of the progressive transitions of the optical power of one or more of the steps increases monotonically.

A21

The ophthalmic lens of one or more of Examples A1 to A19, wherein the rate of change of the progressive transitions of the optical power of one or more of the steps decreases monotonically.

A22

The ophthalmic lens of one or more of Examples A1 to A21, wherein the rate of change of the at least a portion of the optical power of one or more of the steps is flat or substantially flat.

A23

The ophthalmic lens of one or more of Examples A1 to A21, wherein the rate of change of the at least a portion of the optical power of one or more of the steps is zero or substantially flat.

A24

The ophthalmic lens of one or more of Examples A1 to A23, wherein the rate of change of the at least a portion of the optical power of one or more of the steps is rapid and occurs over a junction width of less than 0.3 mm, 0.25 mm, 0.2 mm or 0.15 mm.

A25

The ophthalmic lens of one or more of Examples A1 to A23, wherein the rate of change of the at least a portion of the optical power of one or more of the steps is gradual and occurs over a junction width of between 0.15 and 1 mm, 0.25 and 0.75 mm or 0.3 and 0.5 mm.

A26

The ophthalmic lens of one or more of Examples A1 to A25, wherein the lens is for correction of myopia and control of the progression of myopia.

A27

The ophthalmic lens of one or more of Examples A1 to A25, wherein the lens is for correction of one or more of the following refractive errors of an eye: myopia, hyperopia, astigmatism and presbyopia.

A28

The ophthalmic lens of one or more of Examples A1 to A27, wherein the lens is a contact lens.

A29

The ophthalmic lens of one or more of Examples A1 to A27, wherein the lens is an intraocular lenses.

A30

The ophthalmic lens of one or more of Examples A1 to A29, wherein the lens is improves vision performance or visual performance.

A31

The ophthalmic lens of one or more of Examples A1 to A29, wherein the lens is improves one or more of the following: clarity of vision, degree of doubling, degree of ghosting, distortion, contrast, contrast sensitivity, visual acuity and overall quality of vision.

A32

A method for correction of myopia and control of the progression of myopia using the lens of one or more of examples A1 to A29.

A33

A method for correction of one or more of the following refractive errors of an eye: myopia, hyperopia, astigmatism and presbyopia using the lens of one or more of examples A1 to

A34

A method for improving vision performance or visual performance using the lens of one or more of examples A1 to A29.

A35

A method for improving one or more of the following: clarity of vision, degree of doubling, degree of ghosting, distortion, contrast, contrast sensitivity, visual acuity and overall quality of vision using the lens of one or more of examples A1 to A29.

Example B1

An ophthalmic lens comprising:
an optic zone comprising:
at least one inner portion having at least a first power profile and at least one outer portion having at least a second power profile;
wherein the first power profile of the at least one inner portion has at least a first step, the first step bounded on either side by a first junction and a second junction, the first power profile having a first change in the rate of change of power at the first junction and second change in the rate of change of power at the second junction, and
the second power profile of the at least one outer portion has at least a second step, the second step bounded on either side by a third junction and a fourth junction, the second power profile having a third change in the rate of change of power at the third junction and a fourth change in the rate of change of power at the fourth junction.

B2

The ophthalmic lens of example B1, wherein the at least one inner portion having at least a first step has between one and six, one and five, two and five or two and four steps.

B3

The ophthalmic lens of examples B1 or B2, wherein the at least one inner portion having at least a first step has between one and six, one and five, two and five or two and four steps.

B4

The ophthalmic lens of examples B1 to B2 or B3, wherein the changes in the rate of change of power at the junctions is rapid.

B5

The ophthalmic lens of examples B1 to B2 or B3, wherein the changes in the rate of change of power at the junctions is gradual.

B6

The ophthalmic lens of examples B1 to B4 or B5, wherein the power within the steps one or more of the following: constant, substantially constant, decreasing and increasing.

B7

The ophthalmic lens of examples B1 to B5 or B6, wherein the power within the first step and the power within the second step is equal, substantially equal or unequal.

B8

The ophthalmic lens of examples B1 to B6 or B7, wherein the width of the steps is between 0 mm and 1.5 mm, 0.1 mm and 1.25 mm, 0.1 mm and 1 mm or 0.15 mm and 1 mm.

B9

A method for correction of myopia and control of the progression of myopia using the lens of one or more of examples B1 to B8.

B10

A method for correction of one or more of the following refractive errors of an eye: myopia, hyperopia, astigmatism and presbyopia using the lens of one or more of examples B1 to B8.

B11

A method for improving vision performance or visual performance using the lens of one or more of examples B1 to B8.

B12

A method for improving one or more of the following: clarity of vision, degree of doubling, degree of ghosting, distortion, contrast, contrast sensitivity, visual acuity and overall quality of vision using the lens of one or more of examples B1 to B8.

Example C1

An ophthalmic lens comprising:
an optical zone comprising:
at least one primary area with at least one primary optical power;
at least two secondary areas comprising:
a first secondary area with a first optical power and a second secondary area with a second optical power;
wherein at least one of the first secondary area and the second secondary area is peripheral of the at least one primary area, and the first and second optical powers are more positive than the at least one primary optical power; and
wherein there is a first power transition from the at least one primary optical power to the first optical power having at least a first step and a second power transition from the at least one primary optical power to the second optical power having at least a second step, the steps not including the at least one primary area and the first and second secondary areas, and wherein for at least one of the first step and second step, the magnitude of the rate of change of the power transitions decreases and then increases.

C2

The ophthalmic lens of example C1, wherein the magnitude of the rate of change of the power transitions decreases rapidly and then increases rapidly.

C3

The ophthalmic lens of example C1, wherein the magnitude of the rate of change of the power transitions decreases gradually and then increases gradually.

C4

The ophthalmic lens of examples C1 to C2 or C3, wherein the at least one primary area has a width between 0.2 mm and 2 mm, 0.3 mm and 1.75 mm or 0.4 mm and 1.5 mm.

C5

The ophthalmic lens of examples C1 to C3 or C4, wherein the first and second optical powers are more positive than the at least one primary optical power by an amount up to, 5 D, 4 D or 3 D.

C6

The ophthalmic lens of examples C1 to C4 or C5, wherein at least one of the first secondary area and the second secondary area has a width between 0 mm and 2 mm, 0.1 mm and 1.75 mm or 0.2 mm and 1.5 mm.

C7

The ophthalmic lens of examples C1 to C5 or C6, wherein at least one of the first power transition and the second power transition has between one and six, one and five, two and six, two and five or two and four steps.

C8

The ophthalmic lens of examples C1 to C6 or C7, wherein for at least one of the first step and the second step, the width is between 0 mm and 1.5 mm, 0.1 mm and 1.25 mm, 0.1 mm and 1 mm or 0.15 mm and 1 mm.

C9

The ophthalmic lens of examples C1 to C7 or C8, wherein for at least one of the first step and the second step, the power may be up to 5 D, 4 D or 3 D more positive than the power of the primary area.

C10

The ophthalmic lens of examples C1 to C8 or C9, wherein for at least one of the first step and the second step, the power is up to 5 D, 4 D or 3 D less positive than the power of at least one of the first secondary area and the second secondary area.

C11

A method for correction of myopia and control of the progression of myopia using the lens of one or more of examples C1 to C10.

C12

A method for correction of one or more of the following refractive errors of an eye: myopia, hyperopia, astigmatism and presbyopia using the lens of one or more of examples C1 to C10.

C13

A method for improving vision performance or visual performance using the lens of one or more of examples C1 to C10.

C11

A method for improving one or more of the following: clarity of vision, degree of doubling, degree of ghosting, distortion, contrast, contrast sensitivity, visual acuity and overall quality of vision using the lens of one or more of examples C1 to C10.

D1

An ophthalmic lens comprising:
an optic zone comprising:
at least one central portion having at least a first power profile and at least one peripheral portion having at least a second power profile;
wherein the first power profile of the at least one central portion has at least a first step, the first step bounded on either side by a first junction and a second junction, the first power profile having a first change in the rate of change of power at the first junction and second change in the rate of change of power at the second junction, and
the second power profile of the at least one peripheral portion has at least a second step, the second step bounded on either side by a third junction and a fourth junction, the second power profile having a third change in the rate of change of power at the third junction and a fourth change in the rate of change of power at the fourth junction.

D2

The ophthalmic lens of example D1, wherein the at least one central portion has between one to six, one to five, two to five, two to six, two to four steps, three to five steps or three to six steps.

D3

The ophthalmic lens of examples D1 or D2, wherein the at least one central portion has at least two, three, four, five steps.

D4

The ophthalmic lens of at least one of the preceding examples D1 to D3, wherein the at least one peripheral portion has between one to six, one to five, two to five, two to four steps, three to five steps or three to six steps.

D5

The ophthalmic lens of at least one of the preceding examples D1 to D4, wherein the at least one peripheral portion has at least two, three, four or five steps.

D6

The ophthalmic lens of at least one of the preceding examples D1 to 5, wherein the changes in the rate of change of power at one or more of the junctions is rapid.

D7

The ophthalmic lens of at least one of the proceeding examples D1 to D6, wherein the changes in the rate of change of power at one or more of the junctions is gradual.

D8

The ophthalmic lens of at least one of the preceding examples D1 to D7, wherein a power within one or more of the steps is one or more of the following: constant, substantially constant, decreasing and increasing.

D9

The ophthalmic lens of at least one of the preceding examples D1 to D8, wherein the power within the first step and the power within the second step is equal, substantially equal or unequal.

D10

The ophthalmic lens of at least one of the preceding examples D1 to D9, wherein one or more of the steps have a width that is between 0 mm and 1.5 mm, 0.1 mm and 1.25 mm, 0.1 mm and 1 mm or 0.15 mm and 1 mm.

D11

The ophthalmic lens of at least one of the preceding examples D1 to D10, wherein one or more of the steps have a width that is at least 0.1 mm, 0.15 mm, 0.25 mm, 0.5 mm, 1 mm or 1.25 mm.

D12

The ophthalmic lens of at least one of the preceding examples D1 to D11, wherein the lens is for correction of myopia and/or control of the progression of myopia.

D13

The ophthalmic lens of at least one of the preceding examples D1 to D12, wherein the lens is for correction of presbyopia.

D14

The ophthalmic lens of at least one of the preceding examples D1 to D13, wherein the at least one peripheral portion has at least 4 or 5 radially spaced steps and the at least one central portion has at least 2 or 3 radially spaced steps.

D15

The ophthalmic lens of at least one of the preceding examples D1 to D13, wherein the at least one peripheral portion has between 2 to 6 radially spaced steps and the at least one central portion has between 1 to 2 radially spaced steps.

D16

The ophthalmic lens of at least one of the preceding examples D1 to D13, wherein the at least one peripheral portion has between 2 to 4 radially spaced steps and the at least one central portion has between 2 to 3 radially spaced steps.

E17

An ophthalmic lens comprising:
an optical zone comprising:
at least one primary area with at least one primary optical power;
at least two secondary areas comprising:
a first secondary area with a first optical power and a second secondary area with a second optical power;
wherein at least one of the first secondary area and the second secondary area is peripheral of the at least one primary area, and the first and second optical powers are more positive than the at least one primary optical power; and
wherein there is a first power transition from the at least one primary optical power to the first optical power having at least a first step and a second power transition from the at least one primary optical power to the second optical power having at least a second step, the steps not including the at least one primary area and the first and second secondary areas, and wherein for at least one of the first step and at least one of the second step, the magnitude of the rate of change of the power transitions decreases at the junction before the step and then increases at the junction after the step.

E18

The ophthalmic lens of example E17, wherein for the steps, the magnitude of the rate of change of the power transitions at the junction before the step decreases in one or more of the following ways: moderate, rapid and gradual, and then increases at the junction after the step in one or more of the following ways: moderate, rapid and gradual.

E19

The ophthalmic lens of at least one of examples E17 to E18, wherein the magnitude of the rate of change of the power transitions decreases rapidly at the junction before the step and then increases rapidly at the junction after the step.

E20

The ophthalmic lens of at least one of examples E17 to E18, wherein the magnitude of the rate of change of the power transitions decreases gradually at the junction before the step and then increases gradually at the junction after the step.

E21

The ophthalmic lens of at least one of examples E17 to E18, wherein the magnitude of the rate of change of the power transitions decreases moderately at the junction before the step and then increases moderately at the junction after the step.

E22

The ophthalmic lens of at least one of examples E17 to E21, wherein the at least one primary area has a width between 0.2 mm and 2 mm, 0.3 mm and 1.75 mm or 0.4 mm and 1.5 mm.

E23

The ophthalmic lens of at least one of examples E17 to E22, wherein the first and second optical powers are more positive than the at least one primary optical power by an amount up to 5 D, 4 D or 3 D.

E24

The ophthalmic lens of at least one of examples E17 to E23, wherein at least one of the first secondary area and the second secondary area has a width between 0 mm and 2 mm, 0.1 mm and 1.75 mm or 0.2 mm and 1.5 mm.

E25

The ophthalmic lens of at least one of examples E17 to E24, wherein at least one of the first power transition and the second power transition has between one and six, one and five, two and six, two and five or two and four steps.

E26

The ophthalmic lens of at least one of examples E17 to E25, wherein at least one of the first power transition and the second power transition have between 1 to 5, 2 to 4, 1 to 3, 2 to 3, 2 to 5 or 2 to 6 radially spaced steps.

E27

The ophthalmic lens of at least one of examples E17 to E26, wherein the first power transition and the second power transition have between 1 to 5, 2 to 4, 1 to 3, 2 to 3, 2 to 5 or 2 to 6 radially spaced steps.

E28

The ophthalmic lens of at least one of examples E17 to E27, wherein at least one of the first power transition and the second power transition have between 1 to 5, 2 to 4, 1 to 3, 2 to 3, 2 to 5 or 2 to 6 radially spaced steps between one or more of the secondary areas or between each secondary area.

E29

The ophthalmic lens of at least one of examples E17 to E28, wherein there is at least 2, 3, 4, 5 or 6 radially spaced steps between one or more of the secondary areas or between each secondary area.

E30

The ophthalmic lens of at least one of examples E17 to E29, wherein for at least one of the first step and the second step, the width is between 0 mm and 1.5 mm, 0.1 mm and 1.25 mm, 0.1 mm and 1 mm or 0.15 mm and 1 mm.

E31

The ophthalmic lens of at least one of examples E17 to E30, wherein for at least one of the first step and the second step, the power is up to 5 D, 4 D or 3 D more positive than the power of the primary area.

E32

The ophthalmic lens of at least one of examples E17 to E30, wherein for the first step and the second step, the power is up to 5 D, 4 D or 3 D more positive than the power of the primary area.

E33

The ophthalmic lens of at least one of examples E17 to E32, wherein for at least one of the first step and the second step, the power is up to 5 D, 4 D or 3 D less positive than the power of at least one of the first secondary area and the second secondary area.

E34

The ophthalmic lens of at least one of examples E17 to E32, wherein for the first step and the second step, the power is up to 5 D, 4 D or 3 D less positive than the power of at least one of the first secondary area and the second secondary area.

E35

The ophthalmic lens of at least one of examples E11 to E32, wherein for the first step and the second step, the power is up to 5 D, 4 D or 3 D less positive than the power of the first secondary area and the second secondary area.

E36

The ophthalmic lens of at least one of the preceding examples E17 to E35, wherein the lens is for correction of myopia and/or control of the progression of myopia.

E37

The ophthalmic lens of at least one of the preceding examples E17 to E35, wherein the lens is for correction of presbyopia.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. An ophthalmic lens comprising:
an optic zone comprising:
a primary area; and
at least one central portion having at least a first power profile and at least one peripheral portion having at least a second power profile;
wherein the primary area is located between the at least one central portion and the at least one peripheral portion and an optical power of the primary area is less than the first power profile of the at least one central portion and the second power profile of the at least one peripheral portion;
wherein the first power profile of the at least one central portion has at least a first step, the first step bounded on either side by a first junction and a second junction, the first power profile having a first change in the rate of change of power at the first junction and second change in the rate of change of power at the second junction, and
the second power profile of the at least one peripheral portion has at least a second step, the second step bounded on either side by a third junction and a fourth junction, the second power profile having a third change in the rate of change of power at the third junction and a fourth change in the rate of change of power at the fourth junction.

2. The ophthalmic lens of claim 1, wherein the at least one central portion has between one to six, one to five, two to five, two to six, two to four steps, three to five steps or three to six steps.

3. The ophthalmic lens of claim 1, wherein the at least one central portion has at least two, three, four, or five steps.

4. The ophthalmic lens of claim 1, wherein the at least one peripheral portion has between one to six, one to five, two to five, two to four steps, three to five steps or three to six steps.

5. The ophthalmic lens of claim 1, wherein the at least one peripheral portion has at least two, three, four or five steps.

6. The ophthalmic lens of claim 1, wherein a power within one or more of the steps is one or more of the following: constant, substantially constant, decreasing and increasing.

7. The ophthalmic lens of claim 1, wherein the power within the first step and the power within the second step is equal, substantially equal or unequal.

8. The ophthalmic lens of claim 1, wherein one or more of the steps have a width that is between 0 mm and 1.5 mm, 0.1 mm and 1.25 mm, 0.1 mm and 1 mm or 0.15 mm and 1 mm.

9. The ophthalmic lens of claim 1, wherein one or more of the steps have a width that is at least 0.1 mm, 0.15 mm, 0.25 mm, 0.5 mm, 1 mm or 1.25 mm.

10. The ophthalmic lens of claim 1, wherein the at least one peripheral portion has at least 4 or 5 radially spaced steps and the at least one central portion has at least 2 or 3 radially spaced steps.

11. An ophthalmic lens comprising:
an optical zone comprising:
at least one primary area with at least one primary optical power;
at least two secondary areas comprising:
a first secondary area with a first optical power and a second secondary area with a second optical power;

wherein the at least one primary area is located between the first secondary area and the second secondary area and wherein at least one of the first secondary area and the second secondary area is located centrally to the at least one primary area, and the first and second optical powers are more positive than the at least one primary optical power; and wherein there is a first power transition from the at least one primary optical power to the first optical power having at least a first step and a second power transition from the at least one primary optical power to the second optical power having at least a second step, the steps not including the at least one primary area and the first and second secondary areas, and wherein for at least one of the first step and at least one of the second step, the magnitude of the rate of change of the power transitions decreases at the junction before the step and then increases at the junction after the step.

12. The ophthalmic lens of claim 11, wherein for the steps, the magnitude of the rate of change of the power transitions at the junction before the step decreases in one or more of the following ways: moderate, rapid and gradual, and then increases at the junction after the step in one or more of the following ways: moderate, rapid and gradual.

13. The ophthalmic lens of claim 11, wherein the magnitude of the rate of change of the power transitions decreases rapidly at the junction before the step and then increases rapidly at the junction after the step.

14. The ophthalmic lens of claim 11, wherein the at least one primary area has a width between 0.2 mm and 2 mm, 0.3 mm and 1.75 mm or 0.4 mm and 1.5 mm.

15. The ophthalmic lens of claim 11, wherein the first and second optical powers are more positive than the at least one primary optical power by an amount up to 5 D, 4 D or 3 D.

16. The ophthalmic lens of claim 11, wherein at least one of the first secondary area and the second secondary area has a width between 0 mm and 2 mm, 0.1 mm and 1.75 mm or 0.2 mm and 1.5 mm.

17. The ophthalmic lens of claim 11, wherein at least one of the first power transition and the second power transition has between one and six, one and five, two and six, two and five or two and four steps.

18. The ophthalmic lens of claim 11, wherein for at least one of the first step and the second step, the width is between 0 mm and 1.5 mm, 0.1 mm and 1.25 mm, 0.1 mm and 1 mm or 0.15 mm and 1 mm.

19. The ophthalmic lens of claim 11, wherein for at least one of the first step and the second step, the power is up to 5 D, 4 D or 3 D more positive than the power of the primary area.

20. The ophthalmic lens of claim 11, wherein for at least one of the first step and the second step, the power is up to 5 D, 4 D or 3 D less positive than the power of at least one of the first secondary area and the second secondary area.

* * * * *